(12) United States Patent
Kameishi et al.

(10) Patent No.: US 10,123,777 B2
(45) Date of Patent: Nov. 13, 2018

(54) ULTRASOUND DIAGNOSIS APPARATUS AND ULTRASOUND PROBE

(71) Applicant: Toshiba Medical Systems Corporation, Otawara-shi (JP)

(72) Inventors: Wataru Kameishi, Nasushiobara (JP); Hiroyuki Shibanuma, Yaita (JP); Shuta Fujiwara, Nasushiobara (JP); Satoshi Kamiyama, Otawara (JP); Takayuki Shiina, Otawara (JP); Masaaki Ishitsuka, Nasushiobara (JP); Tomohiro Fujita, Nasushiobara (JP); Teruki Hagihara, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 484 days.

(21) Appl. No.: 14/976,666

(22) Filed: Dec. 21, 2015

(65) Prior Publication Data

US 2016/0106393 A1 Apr. 21, 2016

Related U.S. Application Data

(63) Continuation of application No. PCT/JP2014/065438, filed on Jun. 11, 2014.

(30) Foreign Application Priority Data

Jun. 21, 2013 (JP) ................. 2013-130141

(51) Int. Cl.
*H01L 41/09* (2006.01)
*A61B 8/00* (2006.01)
(Continued)

(52) U.S. Cl.
CPC .............. *A61B 8/4494* (2013.01); *A61B 8/56* (2013.01); *B06B 1/023* (2013.01); *B06B 1/0207* (2013.01);
(Continued)

(58) Field of Classification Search
CPC ....... A61B 8/4494; A61B 8/56; B06B 1/0207; B06B 1/023; B06B 1/0607; G01S 7/5202
(Continued)

(56) References Cited

U.S. PATENT DOCUMENTS

2011/0101824 A1   5/2011   Nishigaki
2012/0294113 A1   11/2012   Amemiya

FOREIGN PATENT DOCUMENTS

JP    2010-81966    4/2010
JP    2011-234848   11/2011
(Continued)

OTHER PUBLICATIONS

International Search Report dated Jul. 8, 2014 in PCT/JP2014/065438, filed Jun. 11, 2014 (with English Translation).

*Primary Examiner* — Thomas Dougherty
(74) *Attorney, Agent, or Firm* — Oblon, McClelland, Maier & Neustadt, L.L.P.

(57) ABSTRACT

An ultrasound diagnosis apparatus includes a transformer, a first power source, a second power source, and a switching unit. The transformer includes a primary winding and a secondary winding, and drives an ultrasound transducer based on a voltage generated in the secondary winding. The first and second power sources cause a potential difference. The switching unit switches a connection path between the primary winding and at least one of the first and second power sources to a first connection path that connects the first power source to one end of the primary winding and the second power source to the other end, a second connection path that connects the first power source to the other end and the second power source to the one end, or a ground connection path that connects the first power source or the second power source to the ground through the primary winding.

12 Claims, 13 Drawing Sheets

(51) Int. Cl.
  *G01S 7/52* (2006.01)
  *B06B 1/02* (2006.01)
  *B06B 1/06* (2006.01)

(52) U.S. Cl.
  CPC .......... *B06B 1/0607* (2013.01); *G01S 7/5202* (2013.01); *B06B 2201/20* (2013.01); *B06B 2201/55* (2013.01)

(58) Field of Classification Search
  USPC ........................................................ 310/317
  See application file for complete search history.

(56) References Cited

FOREIGN PATENT DOCUMENTS

| | | |
|---|---|---|
| JP | 2012-239496 | 12/2012 |
| JP | 2013-106625 | 6/2013 |
| WO | WO 2010/103747 A1 | 9/2010 |

US 10,123,777 B2

ULTRASOUND DIAGNOSIS APPARATUS AND ULTRASOUND PROBE

CROSS-REFERENCE TO RELATED APPLICATION

This application is based upon and claims the benefit of priority from Japanese Patent Application No. 2013-130141, filed Jun. 21, 2013; the entire contents of which are incorporated herein by reference.

FIELD

Embodiments described herein relate generally to an ultrasound diagnosis apparatus and an ultrasound probe.

BACKGROUND

An ultrasound diagnosis apparatus transmits ultrasound waves to a subject by an ultrasound probe including a plurality of ultrasound transducers. The ultrasound diagnosis apparatus generates tomographic image data, three-dimensional image data, and the like of the inside of the subject based on reflected waves (ultrasound echo) from the subject.

The ultrasound diagnosis apparatus may be configured such that the ultrasound transducers are driven by a voltage induced in the secondary winding by a voltage applied when a power source is connected to the primary winding of a transformer. With this configuration, by switching the direction of current applied to the primary winding, the polarity of a pulse induced in the secondary winding can be reversed. The ultrasound diagnosis apparatus configured like this outputs a positive voltage signal, a negative voltage signal corresponding to the positive voltage signal with polarity reversed, and three-level voltage signals of the zero voltage signal to the ultrasound transducers as transmission signals. Besides, the ultrasound diagnosis apparatus having such a configuration variously controls the width of the pulse induced in the secondary winding to control the ultrasound frequency characteristics.

There is Besides known the ultrasound diagnosis apparatus configured to variously control the voltage level of voltage signals using a digital-to-analog converter (DAC) and a linear amplifier to thereby control the ultrasound frequency characteristics.

However, the various control of the pulse width requires a higher clock frequency. Moreover, due to the effect of the rise characteristics of the transmission signals, it is difficult to output transmission signals of wide pulse width and those of narrow pulse width with equal amplitude to the ultrasound transducers.

In addition, the use of DAC and a linear amplifier requires a large transmitter circuit. This necessitates a high cost and large power consumption.

DETAILED DESCRIPTION

In general, according to one embodiment, an ultrasound diagnosis apparatus includes a transformer, a first power source, a second power source, and a switching unit. The transformer includes a primary winding and a secondary winding, and drives an ultrasound transducer based on a voltage generated in the secondary winding. The first power source causes a potential difference with respect to a reference potential of the ground at a first potential that is different from the reference potential. The second power source causes a potential difference with respect to the reference potential at a second potential that is different from the reference potential and the first potential. The switching unit switches a connection path between the primary winding and at least one of the first power source and the second power source to a first connection path that connects the first power source to one end of the primary winding and the second power source to the other end of the primary winding, a second connection path that connects the first power source to the other end of the primary winding and the second power source to the one end of the primary winding, or a ground connection path that connects the first power source or the second power source to the ground through the primary winding.

According to another embodiment, an ultrasound probe includes an ultrasound transducer, a transformer, a first power source, a second power source, and a switching unit. The transformer includes a primary winding and a secondary winding, and drives the ultrasound transducer based on a voltage generated in the secondary winding. The first power source causes a potential difference with respect to a reference potential of the ground at a first potential that is different from the reference potential. The second power source causes a potential difference with respect to the reference potential at a second potential that is different from the reference potential and the first potential. The switching unit switches a connection path between the primary winding and at least one of the first power source and the second power source to a first connection path that connects the first power source to one end of the primary winding and the second power source to the other end of the primary winding, a second connection path that connects the first power source to the other end of the primary winding and the second power source to the one end of the primary winding, or a ground connection path that connects the first power source or the second power source to the ground through the primary winding.

First Embodiment

[Configuration]

Figure 1:
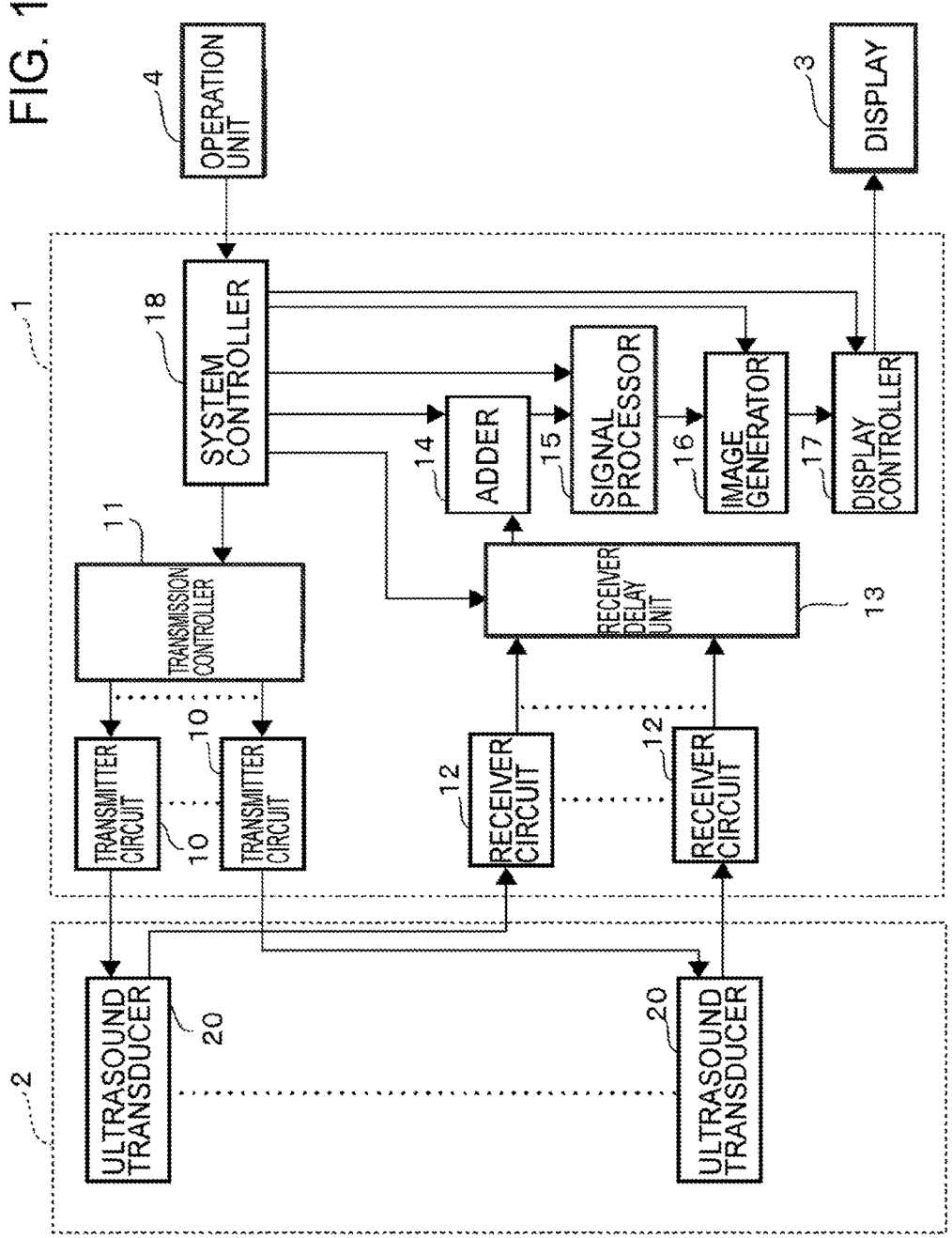
FIG. 1 is a block diagram illustrating the configuration of an ultrasound diagnosis apparatus according to an embodiment.

FIG. 1 is a block diagram illustrating a configuration of an ultrasound diagnosis apparatus according to a first embodiment. The ultrasound diagnosis apparatus includes a main body 1, an ultrasound probe 2, a display 3, and an operation unit 4.

(Main Body 1)

The main body 1 includes a transmitter circuit 10, a transmission controller 11, a receiver circuit 12, a receiver delay unit 13, an adder 14, a signal processor 15, an image generator 16, a display controller 17, and a system controller 18.

(The Transmitter Circuit 10)

Figure 2:
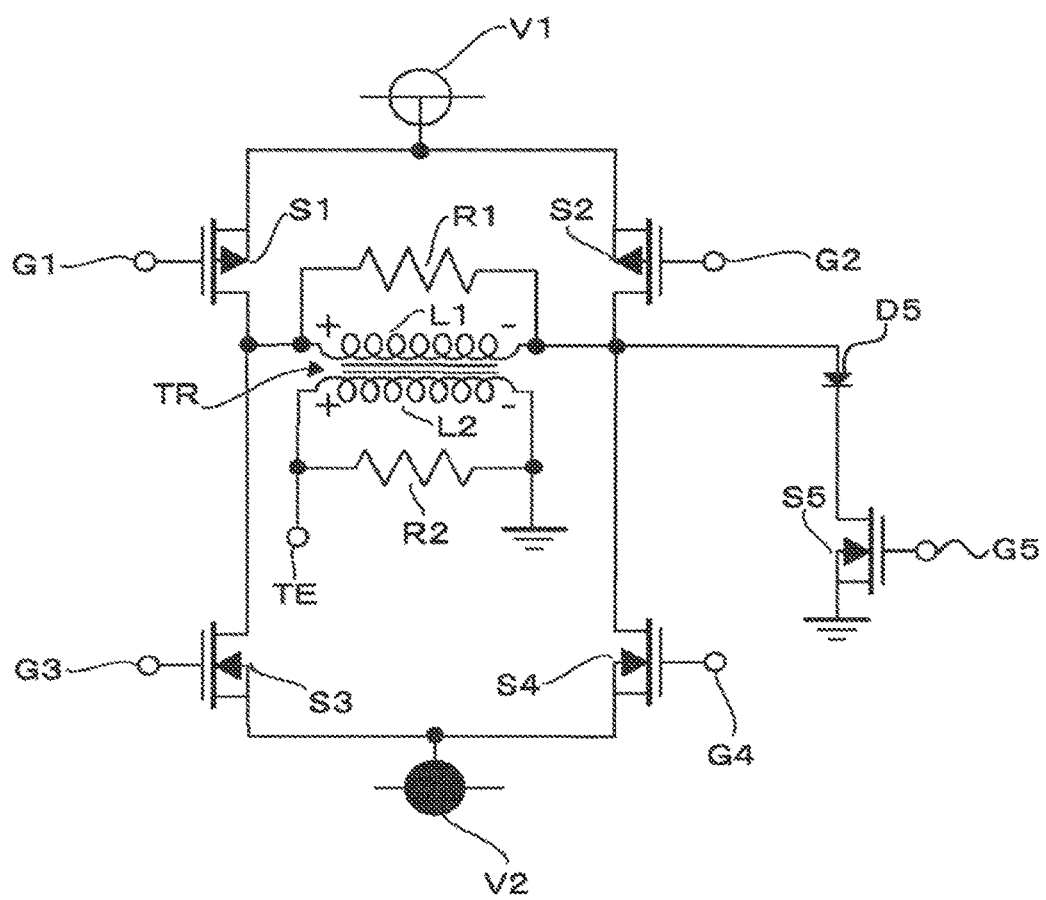
FIG. 2 is a circuit diagram illustrating the configuration of a transmitter circuit of the embodiment.
Figure 3:
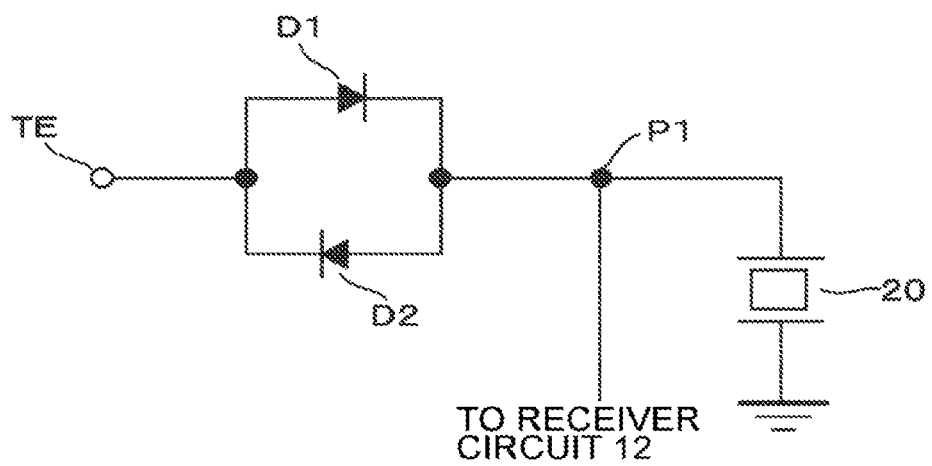
FIG. 3 is a circuit diagram illustrating the configuration the transmitter circuit of the embodiment.

The transmitter circuit 10 is provided for each of ultrasound transducers 20. FIGS. 2 and 3 are circuit diagrams illustrating the configuration of the transmitter circuit 10 of this embodiment. The terminal TE in FIG. 2 is connected to the terminal TE in FIG. 3. The transmitter circuit 10 includes a transformer TR, a first power source V1, a second power source V2, and a switching unit. The transformer TR is provided with a primary winding L1 and a secondary winding L2. It is assumed herein that the primary winding L1 and the secondary winding L2 are wound from the positive end to the negative end thereof. In addition, the positive end of the primary winding L1 is referred to as one end, while the negative end is referred to as the other end. The transformer TR outputs a transmission signal based on a voltage generated in the secondary winding L2 to the ultrasound transducer 20 to drive the ultrasound transducer 20. The first power source V1 causes a potential difference with respect to a reference potential at a first potential different from the reference potential of the ground. For example, the first power source V1 is a positive voltage power source that has a first potential higher than the reference potential to causes a potential difference with respect to the reference potential. In addition, the first power source V1 discharges a current. The second power source V2 causes a potential difference with respect to the reference potential at a second potential different from the reference potential and the first potential. For example, the second power source V2 is a negative voltage power source that has a second potential lower than the reference potential to causes a potential difference with respect to the reference potential. In addition, the second power source V2 sucks a current. Incidentally, to reduce the overshoot of transmission signals, in the transformer TR, for example, a resistor R1 may be arranged in parallel with the primary winding L1, and a resistor R2 may be arranged in parallel with the secondary winding L2.

The switching unit switches a connection path between the primary winding L1 and at least one of the first power source V1 and the second power source V2 to a first connection path that connects the first power source V1 to one end of the primary winding L1 and the second power source V2 to the other end of the primary winding L1, a second connection path that connects the first power source V1 to the other end of the primary winding L1 and the second power source V2 to the one end of the primary winding L1, a short circuit path that causes a short circuit between the one end and the other end of the primary winding L1, or a ground connection path that connects the first power source V1 or the second power source V2 to the ground through the primary winding L1, to generate a changing voltage in the secondary winding L2. The ground connection path includes a first ground connection path, in which a current flows in order of the first power source V1, the one end of the primary winding L1, the other end of the primary winding L1, and the ground as the forward direction.

The switching unit includes a pair of first potential-side switches, a pair of second potential-side switches, and a ground-side switch. The first potential-side switches are located between both ends of the primary winding L1 and the first power source V1. The first potential-side switches can turn on and off the connection between both ends of the primary winding L1 and the first power source V1. Switches S1 and S2 of this embodiment correspond to the first potential-side switches. The second potential-side switches are located between both ends of the primary winding L1 and the second power source V2. The second potential-side switches can turn on and off the connection between both ends of the primary winding L1 and the second power source V2. Switches S3 and S4 of this embodiment correspond to the second potential-side switches. The ground-side switch is located between the other end of the primary winding L1 and the ground. A switch S5 of this embodiment corresponds to the ground-side switch.

The first potential-side switches (the switches S1, S2) are metal-oxide-semiconductor field-effect transistors (MOSFET), in which a current flows from the first power source V1 side to the primary winding L1 side as the forward direction when they are on. More specifically, the first potential-side switches are so-called p-type MOSFETs. The second potential-side switches (the switches S3, S4) are field-effect transistors, in which a current flows from the primary winding L1 side to the second power source V2 side as the forward direction when they are on. More specifically, the second potential-side switches are so-called n-type MOSFETs. The ground-side switch (the switch S5) is located between the other end of the primary winding L1 and the ground in the first ground connection path. The ground-side switch is a field-effect transistor, in which a current flows from the other end of the primary winding L1 side to the ground side as the forward direction when it is on. More specifically, the ground-side switch is so-called n-type MOSFET. The first potential-side switches, the second potential-side switches, and the ground-side switch are described herein as MOSFETs by way of example. However, the first potential-side switches, the second potential-side switches, and the ground-side switch may be switching elements such as bipolar transistors or insulated gate bipolar transistors.

The source of the switch S1 is connected to the first power source V1, and the drain of the switch S1 is connected to the one end of the primary winding L1. Besides, the source of the switch S2 is connected to the first power source V1, and the drain of the switch S2 is connected to the other end of the primary winding L1. The drain of the switch S3 is connected to the one end of the primary winding L1, and the source of the switch S3 is connected to the second power source V2. The drain of the switch S4 is connected to the other end of the primary winding L1, and the source of the switch S4 is connected to the second power source V2. The drain of the switch S5 is connected to the other end of the primary winding L1, and the source of the switch S5 is connected to the ground.

The gates of the switches S1, S2, S3, S4, and S5 are connected to the transmission controller 11. In response to a control signal from the transmission controller 11, the switching unit turns on and off the switches individually to thereby switch the connection path between the primary winding L1 and at least one of the first power source V1 and the second power source V2 to the first connection path, the second connection path, the short circuit path, or the first ground connection path.

A description is given herein of the voltage level of the transmission signal sent to the ultrasound transducer 20 for each connection path. In the description, "V11" represents the voltage of the first power source V1, and "V21" represents the voltage of the second power source V2. It is assumed, for example, that the absolute value of "V11" is greater than the absolute value of "V21". In this example, it is also assumed that, in the transformer TR, a voltage k times as high as the voltage of the primary winding L1 is generated in the secondary winding L2.

When the switching unit turns the switches S1 and S4 on and turns the switches S2, S3, and S5 off, and thereby switches the connection path to the first connection path, a voltage of "k×(V11−V21)" is generated in the secondary winding L2, and a transmission signal at this voltage level is sent to the ultrasound transducer 20. When the switching unit turns the switches S1 and S5 on and turns the switches S2, S3, and S4 off, and thereby switches the connection path to the first ground connection path, a voltage of "k×V11" is generated in the secondary winding L2, and a transmission signal at this voltage level is sent to the ultrasound transducer 20. When the switching unit turns the switches S3 and S4 on and turns the switches S1, S2, and S5 off, and thereby switches the connection path to the short circuit path, the voltage of the primary winding L1 is zero, and also the voltage of the secondary winding L2 is zero. Thus, a transmission signal at this voltage level, i.e., zero voltage, is sent to the ultrasound transducer 20. Further, when the switching unit turns the switches S2 and S3 on and turns the switches S1, S4, and S5 off, and thereby switches the connection path to the second connection path, a voltage of "−k×(V11−V21)" is generated in the secondary winding L2, and a transmission signal at this voltage level is sent to the ultrasound transducer 20. Incidentally, the transmission signal is a signal with a reversed polarity of the transmission signal transmitted when the connection path is the first connection path. By switching the connection path in this manner, the transmitter circuit 10 can output transmission signals at four levels of voltages to the ultrasound transducer 20.

The transmitter circuit 10 may include a diode D5 between the field-effect transistor (the switch S5) of the first ground connection path and the other end of the primary winding L1. The forward direction of the diode D5 is a direction from the other end of the primary winding L1 to the ground. Thus, the diode D5 protects the switch S5 from reverse voltage.

The ultrasound transducer 20 is connected to one end of the secondary winding L2 and the receiver circuit 12. A connecting portion of wiring, which is connected to the ultrasound transducer 20, the one end of the secondary winding L2, and the receiver circuit 12, is referred to as connection point P1. The other end of the secondary winding L2 is connected to the ground. Between the one end of the secondary winding L2 and the connection point P1, a diode switch formed of the diodes D1 and D2 is located. The diodes D1 and D2 are arranged such that the anode terminal and the cathode terminal are connected to the same wiring.

When the amplitude of a received signal is equal to or greater than a threshold, the diodes D1 and D2 turn on and allow the signal to pass through. When the amplitude is less than the threshold, the diodes D1 and D2 turn off and block the signal. In general, the amplitude of the transmission signal sent to the ultrasound transducer 20 is greater than that of the echo signal output from the ultrasound transducer 20. The threshold of the diodes D1 and D2 is a value between the amplitude of the transmission signal and that of the echo signal. Thereby, the transmission signal is sent through the diode switch to the ultrasound transducer 20. On the other hand, the echo signal is blocked by the diode switch, and is sent to the receiver circuit 12.

A limiter (not illustrated) may be arranged between the connection point P1 and the receiver circuit 12. The limiter limits the passage of signals with a predetermined amplitude or more. In other words, the limiter allows signals of an amplitude less than the threshold to pass through. Thereby, the limiter prevents the transmission signal from being sent to the receiver circuit 12.

(Transmission Controller 11)

The transmission controller 11 outputs a control signal to gate G1 of the switch S1, gate G2 of the switch S2, gate G3 of the switch S3, gate G4 of the switch S4, and gate G5 of the switch S5 of the switching unit individually to turn on and off each of the switches S1, S2, S3, S4, and S5 individually.

(Receiver Circuit 12)

The receiver circuit 12 is provided for each of the ultrasound transducers 20. The receiver circuit 12 includes a preamplifier circuit and an analog-to-digital (A/D) converter (not illustrated). The preamplifier circuit amplifies an echo signal received from the ultrasound transducer 20. The A/D converter converts the echo signal amplified into a digital signal, and outputs it to the receiver delay unit 13.

(Receiver Delay Unit 13)

The receiver delay unit 13 assigns the digital signal received from the receiver circuit 12 a delay time required to determine the reception directivity, and outputs it to the adder 14.

(Adder 14)

The adder 14 adds the digital signal that is assigned a delay time. This addition emphasizes a reflection component from a direction corresponding to the reception directivity. The adder 14 outputs the digital signal added as a reception signal to the signal processor 15.

(Signal Processor 15)

The signal processor 15 includes a B-mode processor. The B-mode processor receives the reception signal from the adder 14 and visualizes the amplitude of the reception signal. For example, the B-mode processor performs band-pass filtering on the reception signal, and detects the envelope of the signal. Then, the B-mode processor compresses the detected data by logarithmic conversion.

The signal processor 15 may include a Doppler processor. The Doppler processor obtains a Doppler shift frequency component by phase detection of the reception signal, and generates a Doppler frequency distribution that represents the blood flow velocity by applying the fast Fourier transform (FFT) to the signal.

In addition, the signal processor 15 may include a color flow mapping (CFM) processor. The CFM processor performs the imaging of blood flow information. The blood flow information includes information of, for example, speed, distribution, power, or the like.

The signal processor 15 outputs the reception signal (ultrasound raster data) having been subjected to signal processing to the image generator 16.

(Image Generator 16)

Having received the reception signal (ultrasound raster data) having been subjected to signal processing from the signal processor 15, the image generator 16 generates ultrasound image data. The image generator 16 includes, for example, a digital scan converter (DSC). The image generator 16 converts the reception signal after the signal processing represented by a series of scan line signals into the image data represented by the Cartesian coordinate system (scan conversion). For example, the B-mode processor of the image generator 16 performs scan conversion on the reception signal after the signal processing to generate B-mode image data representing the morphology of a tissue of the subject. The image generator 16 outputs the ultrasound image data to the display controller 17.

(Display Controller 17)

Having received the ultrasound image data from the image generator 16, the display controller 17 displays an ultrasound image on the display 3 based on the ultrasound image data.

(System Controller 18)

The system controller 18 controls each unit of the ultrasound diagnosis apparatus. The system controller 18 includes, for example, a storage and a processor. The storage stores computer programs for implementing the functions of each unit of the ultrasound diagnosis apparatus. The processor executes the computer programs to implement the functions.

(Ultrasound Probe 2)

The ultrasound probe 2 transmits ultrasound waves to the subject, and receives reflected waves from the subject. The ultrasound probe 2 may be a one-dimensional array probe including a plurality of ultrasound transducers (20) arrayed in the scanning direction, or a two-dimensional array probe including two-dimensional arrays of a plurality of ultrasound transducers (20). In addition, a mechanical one-dimensional array probe may also be used, in which a plurality of ultrasound transducers (20) are arrayed in the scanning direction, and vibrated in a direction perpendicular to the scanning direction.

(Ultrasound Transducer 20)

The ultrasound probe 2 includes a plurality of the ultrasound transducers 20. The ultrasound transducer 20 each include a piezoelectric element and a pair of electrodes sandwiching the piezoelectric element. The ultrasound transducer 20 receives a transmission signal from the transmitter circuit 10, and applies a voltage based on the transmission signal received to generate an ultrasound wave. The ultrasound transducer 20 receives reflected waves from the subject, and outputs an echo signal to the receiver circuit 12.

(Display 3)

The display 3 displays the ultrasound image. The display 3 includes, for example, a display device such as a cathode ray tube (CRT) or a liquid crystal display (LCD). The display 3 need not necessarily be integrated with the ultrasound diagnosis apparatus, and may be configured to display the ultrasound image as being controlled by the display controller 17 through a common interface.

(Operation Unit 4)

The operation unit 4 is operated by a user and feeds each unit of the apparatus with signals or information corresponding to the operation. The operation unit 4 includes, for example, a keyboard, a mouse, a touch panel, and the like. Besides, the operation unit 4 need not necessarily be integrated with the ultrasound diagnosis apparatus, and may be configured to feed each unit of the apparatus with signals or information through a common interface.

[Operation]

Figure 4:
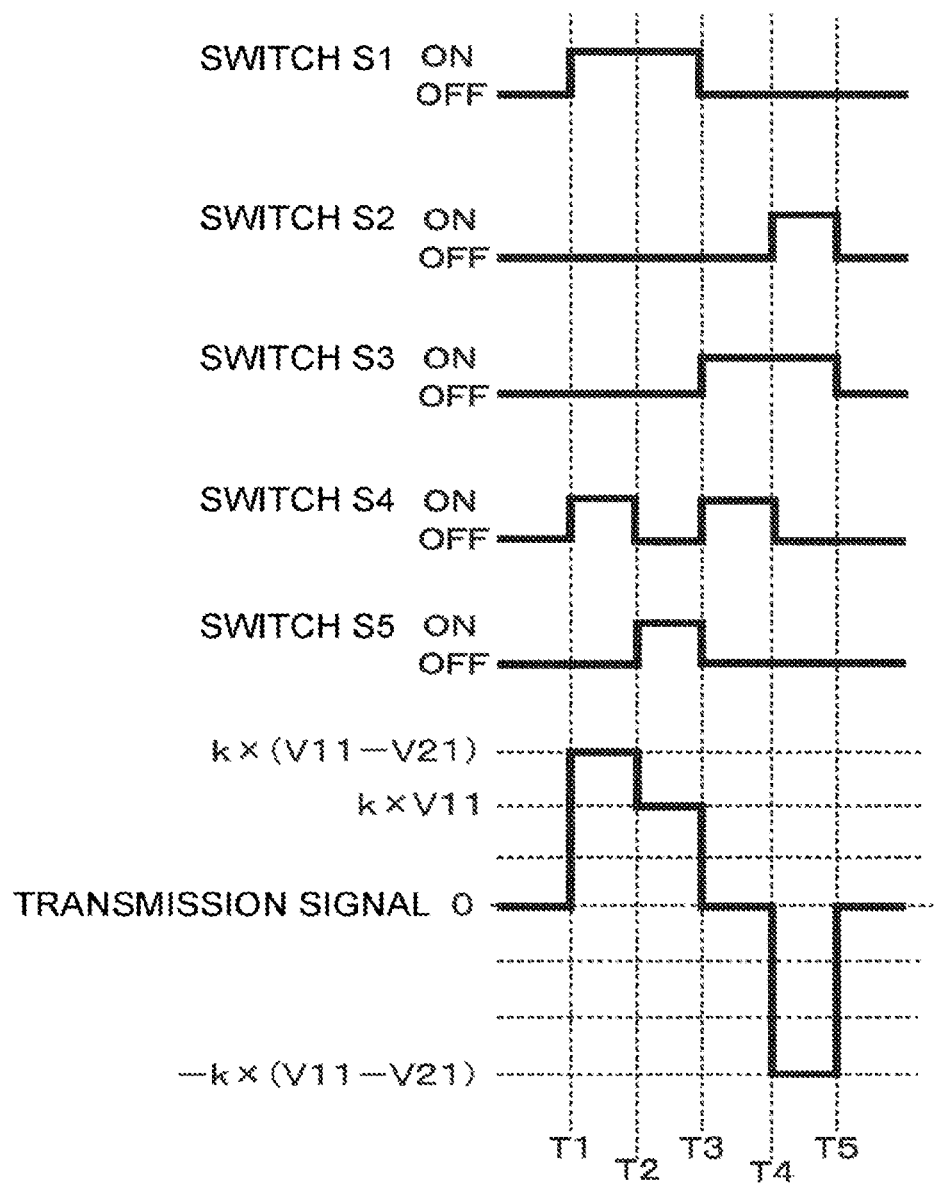
FIG. 4 is a timing chart illustrating an example of the operation of the ultrasound diagnosis apparatus of the embodiment.

FIG. 4 is a timing chart illustrating an example of the operation of the transmitter circuit 10 of the ultrasound diagnosis apparatus according to this embodiment. The timing chart illustrates the relationship between the on/off state of each switch and the voltage level of the transmission signal.

From time T1 to time T2, according to a control signal from the transmission controller 11, the switching unit makes the switches S1 and S4 on, and makes the switches S2, S3, and S5 off. Thereby, the connection path is switched to the first connection path. At this time, a voltage of "k×(V11−V21)" is generated in the secondary winding L2, and a transmission signal at this voltage level is sent to the ultrasound transducer 20.

From time T2 to time T3, according to a control signal from the transmission controller 11, the switching unit makes the switches S1 and S5 on, and makes the switches S2, S3 and S4 off. Thereby, the connection path is switched to the first ground connection path. At this time, a voltage of "k×V11" is generated in the secondary winding L2, and a transmission signal at this voltage level is sent to the ultrasound transducer 20.

From time T3 to time T4, according to a control signal from the transmission controller 11, the switching unit makes the switches S3 and S4 on, and makes the switches S1, S2, and S5 off. Thereby, the connection path is switched to the short circuit path. At this time, the voltage of the primary winding L1 is zero, and also the voltage of the secondary winding L2 is zero. Thus, a transmission signal at this voltage level, i.e., zero voltage, is sent to the ultrasound transducer 20.

From time T4 to time T5, according to a control signal from the transmission controller 11, the switching unit makes the switches S2 and S3 on, and makes the switches S1, S4, and S5 off. Thereby, the connection path is switched to the second connection path. At this time, a voltage of "−k×(V11−V21)" is generated in the secondary winding L2, and a transmission signal at this voltage level is sent to the ultrasound transducer 20.

According to this embodiment, the ultrasound diagnosis apparatus includes a transformer TR, a first power source V1, a second power source V2, and a switching unit. The transformer TR is provided with a primary winding L1 and a secondary winding L2, and drives the ultrasound transducer 20 based on the voltage generated in the secondary winding L2. The switching unit switches the connection path between the primary winding L1 and at least one of the first power source V1 and the second power source V2 to the first connection path that connects the first power source V1 to one end of the primary winding L1 and the second power source V2 to the other end of the primary winding L1, the second connection path that connects the first power source V1 to the other end of the primary winding L1 and the second power source V2 to the one end of the primary winding L1, the short circuit path that causes a short circuit between the one end and the other end of the primary winding L1, or the ground connection path that connects the first power source V1 or the second power source V2 to the ground through the primary winding L1, thereby generating voltages of different levels in the secondary winding L2. The ground connection path includes the first ground connection path, in which a current flows in order of the first power source V1, the one end of the primary winding L1, the other end of the primary winding L1, and the ground as the forward direction. Thus, the ultrasound diagnosis apparatus of this embodiment outputs transmission signals at various voltage levels from the transmitter circuit 10 that includes the one first power source V1 and the one second power source V2. Thereby, the small-scale transmitter circuit 10 can output transmission signals of different voltage levels to the ultrasound transducer 20.

Modification 1 of First Embodiment

[Configuration]

Figure 5:
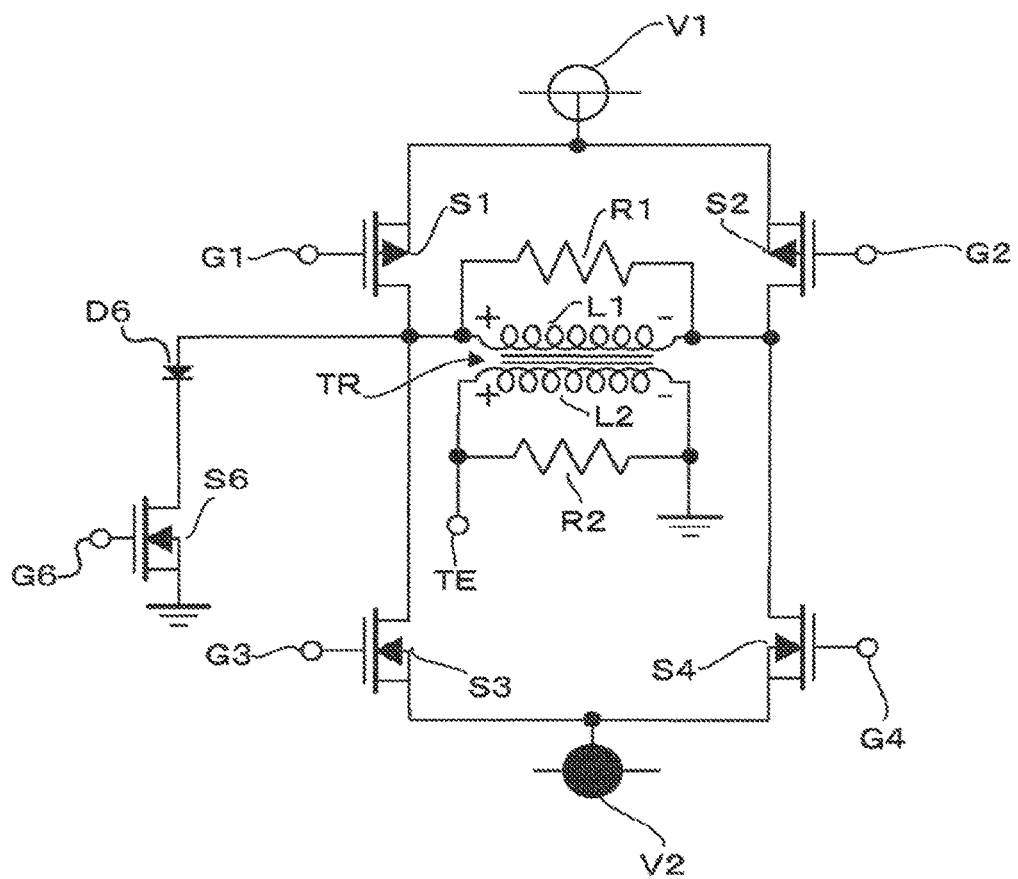
FIG. 5 is a circuit diagram illustrating the configuration of a transmitter circuit according to a modification of the embodiment.

This modification is different from the first embodiment in the configuration of the switching unit of the transmitter circuit 10 and the transmission controller 11. In the following, the differences are described. FIGS. 3 and 5 are circuit diagrams illustrating the configuration of the transmitter circuit 10 of this modification. The terminal TE in FIG. 3 is connected to the terminal TE in FIG. 5.

The switching unit switches the connection path between the primary winding L1 and at least one of the first power source V1 and the second power source V2 to the first connection path that connects the first power source V1 to one end of the primary winding L1 and the second power source V2 to the other end of the primary winding L1, the second connection path that connects the first power source V1 to the other end of the primary winding L1 and the second power source V2 to the one end of the primary winding L1, the short circuit path that causes a short circuit between the one end and the other end of the primary winding L1, or the ground connection path that connects the first power source V1 or the second power source V2 to the ground through the primary winding L1, thereby generating voltages of different levels in the secondary winding L2. The ground connection path includes a second ground connection path, in which a current flows in order of the first power source V1, the other end of the primary winding L1, the one end of the primary winding L1, and the ground as the forward direction.

The switching unit includes a pair of first potential-side switches, a pair of second potential-side switches, and a ground-side switch. The first potential-side switches are located between both ends of the primary winding L1 and the first power source V1. The switches S1 and S2 of this modification correspond to the first potential-side switches. The second potential-side switches are located between both ends of the primary winding L1 and the second power source V2. The switches S3 and S4 of this modification correspond to the second potential-side switches. The ground-side switch is located between the one end of the primary winding L1 and the ground. A switch S6 of this modification corresponds to the ground-side switch.

The first potential-side switches (the switches S1, S2) are field-effect transistors, in which a current flows from the first power source V1 side to the primary winding L1 side as the forward direction when they are on. More specifically, the first potential-side switches are so-called p-type MOSFETs. The second potential-side switches (the switches S3, S4) are field-effect transistors, in which a current flows from the primary winding L1 side to the second power source V2 side as the forward direction when they are on. More specifically, the second potential-side switches are so-called n-type MOSFETs. The ground-side switch (the switch S6) is arranged between the one end of the primary winding L1 and the ground in the second ground connection path. The ground-side switch is a field-effect transistor, in which a current flows from the one end of the primary winding L1 side to the ground side as the forward direction when it is on. More specifically, the ground-side switch is so-called n-type MOSFET.

The source of the switch S1 is connected to the first power source V1, and the drain of the switch S1 is connected to the one end of the primary winding L1. Besides, the source of the switch S2 is connected to the first power source V1, and the drain of the switch S2 is connected to the other end of the primary winding L1. The drain of the switch S3 is connected to the one end of the primary winding L1, and the source of the switch S3 is connected to the second power source V2. The drain of the switch S4 is connected to the other end of the primary winding L1, and the source of the switch S4 is connected to the second power source V2. The drain of the switch S6 is connected to the one end of the primary winding L1, and the source of the switch S6 is connected to the ground.

When the switching unit turns the switches S1 and S4 on and turns the switches S2, S3, and S6 off, and thereby switches the connection path to the first connection path, a voltage of "k×(V11−V21)" is generated in the secondary winding L2, and a transmission signal at this voltage level is sent to the ultrasound transducer 20. When the switching unit turns the switches S3 and S4 on and turns the switches S1, S2, and S6 off, and thereby switches the connection path to the short circuit path, the voltage of the primary winding L1 is zero, and also the voltage of the secondary winding L2 is zero. Thus, a transmission signal at this voltage level, i.e., zero voltage, is sent to the ultrasound transducer 20. When the switching unit turns the switches S2 and S6 on and turns the switches S1, S3, and S4 off, and thereby switches the connection path to the second ground connection path, a voltage of "−k×V11" is generated in the secondary winding L2, and a transmission signal at this voltage level is sent to the ultrasound transducer 20. Further, when the switching unit turns the switches S2 and S3 on and turns the switches S1, S4, and S6 off, and thereby switches the connection path to the second connection path, a voltage of "−k×(V11−V21)" is generated in the secondary winding L2, and a transmission signal at this voltage level is sent to the ultrasound transducer 20. Incidentally, the transmission signal is a signal with a reversed polarity of the transmission signal transmitted when the connection path is the first connection path. By switching the connection path in this manner, the transmitter circuit 10 can output transmission signals at four levels of voltages to the ultrasound transducer 20.

The transmitter circuit 10 may further include a diode D6 between the field-effect transistor (the switch S6) of the second ground connection path and the one end of the primary winding L1. The forward direction of the diode D6 is a direction from the one end of the primary winding L1 to the ground. Thus, the diode D6 protects the switch S6 from reverse voltage.

The transmission controller 11 outputs a control signal to the gate G1 of the switch S1, the gate G2 of the switch S2, the gate G3 of the switch S3, the gate G4 of the switch S4, and gate G6 of the switch S6 of the switching unit individually to turn on and off each of the switches S1, S2, S3, S4, and S6 individually.

[Operation]

Figure 6:
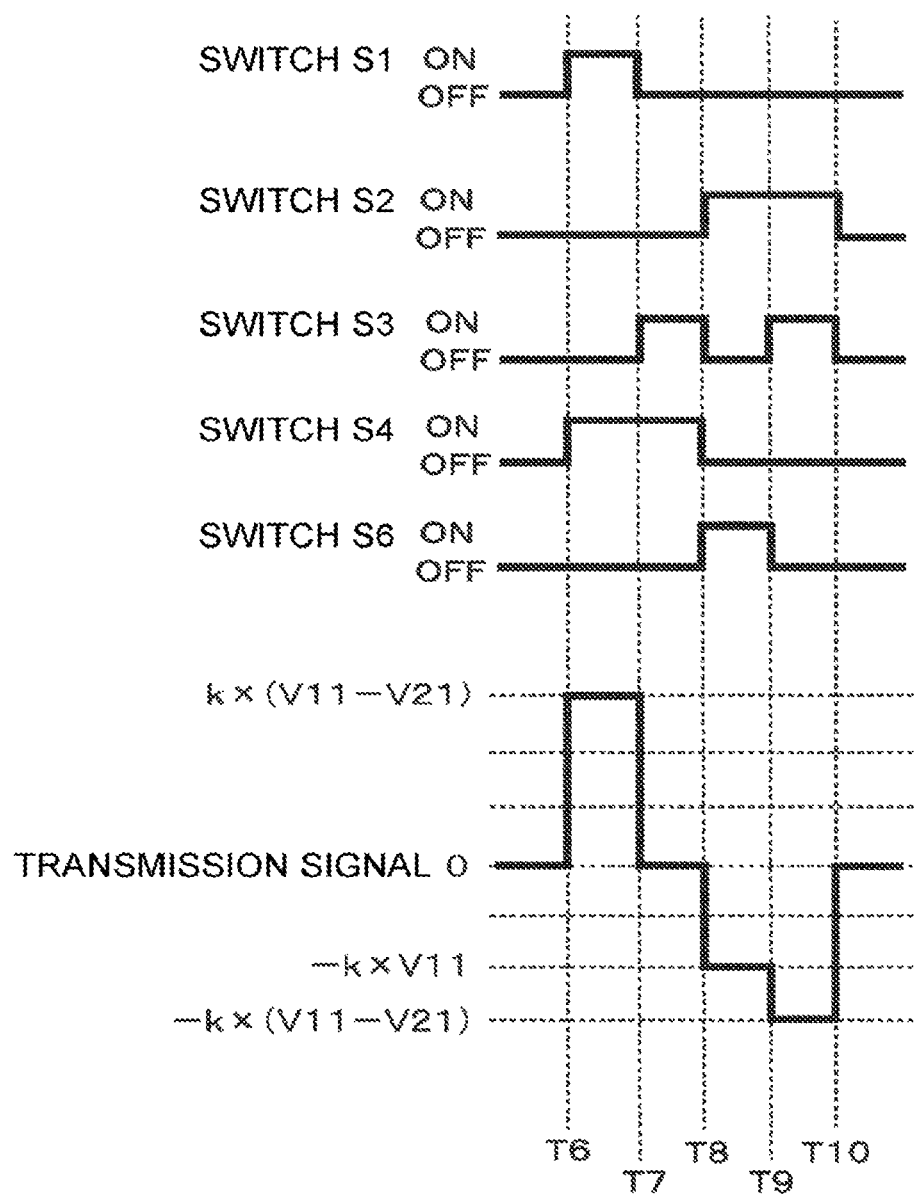
FIG. 6 is a timing chart illustrating an example of the operation of an ultrasound diagnosis apparatus of the modification.

FIG. 6 is a timing chart illustrating an example of the operation of the transmitter circuit 10 of the ultrasound diagnosis apparatus of this modification. The timing chart illustrates the relationship between the on/off state of each switch and the voltage level of the transmission signal.

From time T6 to time T7, according to a control signal from the transmission controller 11, the switching unit makes the switches S1 and S4 on, and makes the switches S2, S3, and S6 off. Thereby, the connection path is switched to the first connection path. At this time, a voltage of "k×(V11−V21)" is generated in the secondary winding L2, and a transmission signal at this voltage level is sent to the ultrasound transducer 20.

From time T7 to time T8, according to a control signal from the transmission controller 11, the switching unit makes the switches S3 and S4 on, and makes the switches S1, S2, and S6 off. Thereby, the connection path is switched to the short circuit path. At this time, the voltage of the primary winding L1 is zero, and also the voltage of the secondary winding L2 is zero. Thus, a transmission signal at this voltage level, i.e., zero voltage, is sent to the ultrasound transducer 20.

From time T8 to time T9, according to a control signal from the transmission controller 11, the switching unit makes the switches S2 and S6 on, and makes the switches S1, S3, and S4 off. Thereby, the connection path is switched to the second ground connection path. At this time, a voltage of "−k×V11" is generated in the secondary winding L2, and a transmission signal at this voltage level is sent to the ultrasound transducer 20.

From time T9 to time T10, according to a control signal from the transmission controller 11, the switching unit makes the switches S2 and S3 on, and makes the switches S1, S4, and S6 off. Thereby, the connection path is switched to the second connection path. At this time, a voltage of "−k×(V11−V21)" is generated in the secondary winding L2, and a transmission signal at this voltage level is sent to the ultrasound transducer 20.

According to this modification, the ultrasound diagnosis apparatus includes a transformer TR, a first power source V1, a second power source V2, and a switching unit. The transformer TR is provided with a primary winding L1 and a secondary winding L2, and drives the ultrasound transducer 20 based on the voltage generated in the secondary winding L2. The switching unit switches the connection path between the primary winding L1 and at least one of the first power source V1 and the second power source V2 to the first connection path that connects the first power source V1 to one end of the primary winding L1 and the second power source V2 to the other end of the primary winding L1, the second connection path that connects the first power source V1 to the other end of the primary winding L1 and the second power source V2 to the one end of the primary winding L1, the short circuit path that causes a short circuit between the one end and the other end of the primary winding L1, or the ground connection path that connects the first power source V1 or the second power source V2 to the ground through the primary winding L1, thereby generating voltages of different levels in the secondary winding L2. The ground connection path includes the second ground connection path, in which a current flows in order of the first power source V1, the other end of the primary winding L1, the one end of the primary winding L1, and the ground as the forward direction. Thus, the ultrasound diagnosis apparatus of this modification outputs transmission signals at various voltage levels from the transmitter circuit 10 that includes the one first power source V1 and the one second power source V2. Thereby, the small-scale transmitter circuit 10 can output transmission signals of different voltage levels to the ultrasound transducer 20.

Modification 2 of First Embodiment

[Configuration]

Figure 7:
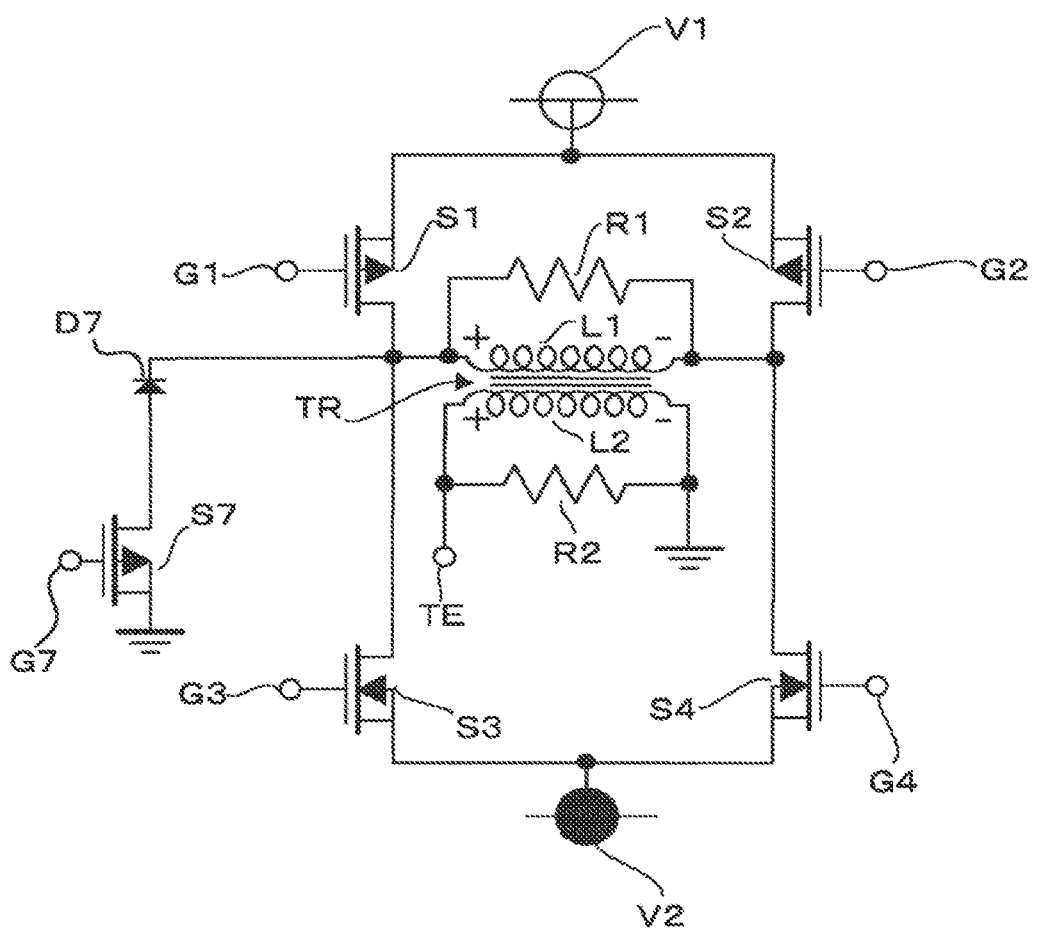
FIG. 7 is a circuit diagram illustrating the configuration of a transmitter circuit according to another modification of the embodiment.

This modification is different from the first embodiment and the modification 1 thereof in the configuration of the switching unit of the transmitter circuit 10 and the transmission controller 11. In the following, the differences are described. FIGS. 3 and 7 are circuit diagrams illustrating the configuration of the transmitter circuit 10 of this modification. The terminal TE in FIG. 3 is connected to the terminal TE in FIG. 7.

The switching unit switches the connection path between the primary winding L1 and at least one of the first power source V1 and the second power source V2 to the first connection path that connects the first power source V1 to one end of the primary winding L1 and the second power source V2 to the other end of the primary winding L1, the second connection path that connects the first power source V1 to the other end of the primary winding L1 and the second power source V2 to the one end of the primary winding L1, the short circuit path that causes a short circuit between the one end and the other end of the primary winding L1, or the ground connection path that connects the first power source V1 or the second power source V2 to the ground through the primary winding L1, thereby generating voltages of different levels in the secondary winding L2. The ground connection path includes a third ground connection path, in which a current flows in order of the ground, the one end of the primary winding L1, the other end of the primary winding L1, and the second power source V2 as the forward direction.

The switching unit includes a pair of first potential-side switches, a pair of second potential-side switches, and a ground-side switch. The first potential-side switches are located between both ends of the primary winding L1 and the first power source V1. The switches S1 and S2 of this modification correspond to the first potential-side switches. The second potential-side switches are located between both ends of the primary winding L1 and the second power source V2. The switches S3 and S4 of this modification correspond to the second potential-side switches. The ground-side switch is located between the one end of the primary winding L1 and the ground. A switch S7 of this modification corresponds to the ground-side switch.

The first potential-side switches (the switches S1, S2) are field-effect transistors, in which a current flows from the first power source V1 side to the primary winding L1 side as the forward direction when they are on. More specifically, the first potential-side switches are so-called p-type MOSFETs. The second potential-side switches (the switches S3, S4) are field-effect transistors, in which a current flows from the primary winding L1 side to the second power source V2 side as the forward direction when they are on. More specifically, the second potential-side switches are so-called n-type MOSFETs. The ground-side switch (the switch S7) is arranged between the one end of the primary winding L1 and the ground in the third ground connection path. The ground-side switch is a field-effect transistor, in which a current flows from the ground side to the one end of the primary winding L1 side as the forward direction when it is on. More specifically, the ground-side switch is so-called p-type MOSFET.

The source of the switch S1 is connected to the first power source V1, and the drain of the switch S1 is connected to the one end of the primary winding L1. Besides, the source of the switch S2 is connected to the first power source V1, and the drain of the switch S2 is connected to the other end of the primary winding L1. The drain of the switch S3 is connected to the one end of the primary winding L1, and the source of the switch S3 is connected to the second power source V2. The drain of the switch S4 is connected to the other end of the primary winding L1, and the source of the switch S4 is connected to the second power source V2. The drain of the switch S7 is connected to the one end of the primary winding L1, and the source of the switch S7 is connected to the ground.

When the switching unit turns the switches S1 and S4 on and turns the switches S2, S3, and S6 off, and thereby switches the connection path to the first connection path, a voltage of "k×(V11−V21)" is generated in the secondary winding L2, and a transmission signal at this voltage level is sent to the ultrasound transducer 20. Further, when the switching unit turns the switches S4 and S7 on and turns the switches S1, S2, and S3 off, and thereby switches the connection path to the third ground connection path, a voltage of "−k×V21" is generated in the secondary winding L2, and a transmission signal at this voltage level is sent to the ultrasound transducer 20. When the switching unit turns the switches S3 and S4 on and turns the switches S1, S2, and S7 off, and thereby switches the connection path to the short circuit path, the voltage of the secondary winding L2 is zero, and a transmission signal at this voltage level, i.e., zero voltage, is sent to the ultrasound transducer 20. When the switching unit turns the switches S3 and S4 on and turns the switches S1, S2, and S7 off, and thereby switches the connection path to the short circuit path, the voltage of the primary winding L1 is zero, and also the voltage of the secondary winding L2 is zero. Thus, a transmission signal at this voltage level, i.e., zero voltage, is sent to the ultrasound transducer 20. Further, when the switching unit turns the switches S2 and S3 on and turns the switches S1, S4, and S7 off, and thereby switches the connection path to the second connection path, a voltage of "−k×(V11−V21)" is generated in the secondary winding L2, and a transmission signal at this voltage level is sent to the ultrasound transducer 20. Incidentally, the transmission signal is a signal with a reversed polarity of the transmission signal transmitted when the connection path is the first connection path. By switching the connection path in this manner, the transmitter circuit 10 can output transmission signals at four levels of voltages to the ultrasound transducer 20.

The transmitter circuit 10 may further include a diode D7 between the field-effect transistor (the switch S7) of the third ground connection path and the one end of the primary winding L1. The forward direction of the diode D7 is a direction from the ground to the one end of the primary winding L1. As a result, the diode D7 protects the switch S7 from reverse voltage.

The transmission controller 11 outputs a control signal to the gate G1 of the switch S1, the gate G2 of the switch S2, the gate G3 of the switch S3, the gate G4 of the switch S4, and gate G7 of the switch S7 of the switching unit individually to turn on and off each of the switches S1, S2, S3, S4, and S7 individually.

[Operation]

Figure 8:
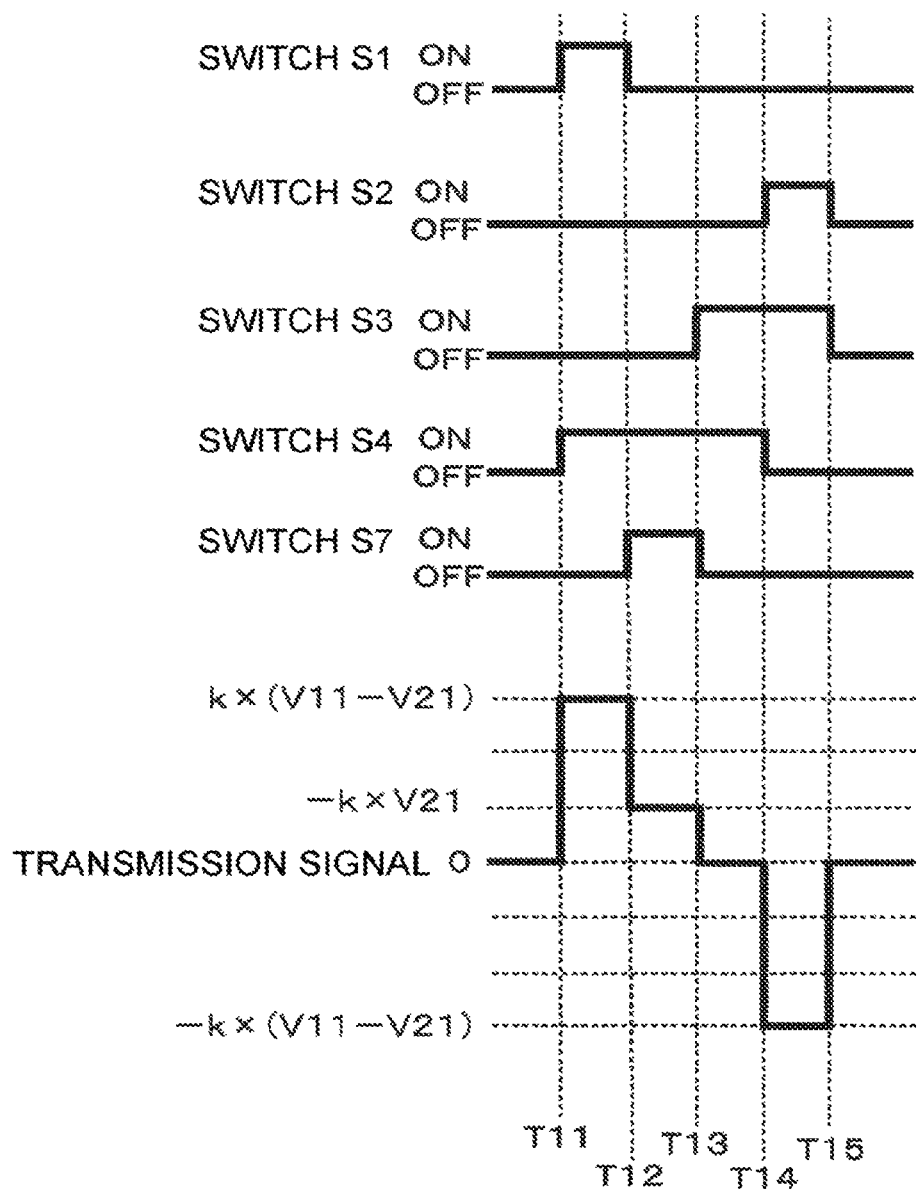
FIG. 8 is a timing chart illustrating an example of the operation of an ultrasound diagnosis apparatus of the modification.

FIG. 8 is a timing chart illustrating an example of the operation of the transmitter circuit 10 of the ultrasound diagnosis apparatus of this modification. The timing chart illustrates the relationship between the on/off state of each switch and the voltage level of the transmission signal.

From time T11 to time T12, according to a control signal from the transmission controller 11, the switching unit makes the switches S1 and S4 on, and makes the switches S2, S3, and S7 off. Thereby, the connection path is switched to the first connection path. At this time, a voltage of "k×(V11−V21)" is generated in the secondary winding L2, and a transmission signal at this voltage level is sent to the ultrasound transducer 20.

From time T12 to time T13, according to a control signal from the transmission controller 11, the switching unit makes the switches S4 and S7 on, and makes the switches S1, S2, and S3 off. Thereby, the connection path is switched to the third ground connection path. At this time, a voltage of "−k×V21" is generated in the secondary winding L2, and a transmission signal at this voltage level is sent to the ultrasound transducer 20.

From time T13 to time T14, according to a control signal from the transmission controller 11, the switching unit makes the switches S3 and S4 on, and makes the switches S1, S2, and S7 off. Thereby, the connection path is switched to the short circuit path. At this time, the voltage of the primary winding L1 is zero, and also the voltage of the secondary winding L2 is zero. Thus, a transmission signal at this voltage level, i.e., zero voltage, is sent to the ultrasound transducer 20.

From time T14 to time T15, according to a control signal from the transmission controller 11, the switching unit makes the switches S2 and S3 on, and makes the switches S1, S4, and S7 off. Thereby, the connection path is switched to the second connection path. At this time, a voltage of "−k×(V11−V21)" is generated in the secondary winding L2, and a transmission signal at this voltage level is sent to the ultrasound transducer 20.

According to this modification, the ultrasound diagnosis apparatus includes a transformer TR, a first power source V1, a second power source V2, and a switching unit. The transformer TR is provided with a primary winding L1 and a secondary winding L2, and drives the ultrasound transducer 20 based on the voltage generated in the secondary winding L2. The switching unit switches the connection path between the primary winding L1 and at least one of the first power source V1 and the second power source V2 to the first connection path that connects the first power source V1 to one end of the primary winding L1 and the second power source V2 to the other end of the primary winding L1, the second connection path that connects the first power source V1 to the other end of the primary winding L1 and the second power source V2 to the one end of the primary winding L1, the short circuit path that causes a short circuit between the one end and the other end of the primary winding L1, or the ground connection path that connects the first power source V1 or the second power source V2 to the ground through the primary winding L1, thereby generating voltages of different levels in the secondary winding L2. The ground connection path includes the third ground connection path, in which a current flows in order of the ground, the one end of the primary winding L1, the other end of the primary winding L1, and the second power source V2 as the forward direction. Thus, the ultrasound diagnosis apparatus of this modification outputs transmission signals at various voltage levels from the transmitter circuit 10 that includes the one first power source V1 and the one second power source V2. Thereby, the small-scale transmitter circuit 10 can output transmission signals of different voltage levels to the ultrasound transducer 20.

Modification 3 of First Embodiment

[Configuration]

Figure 9:
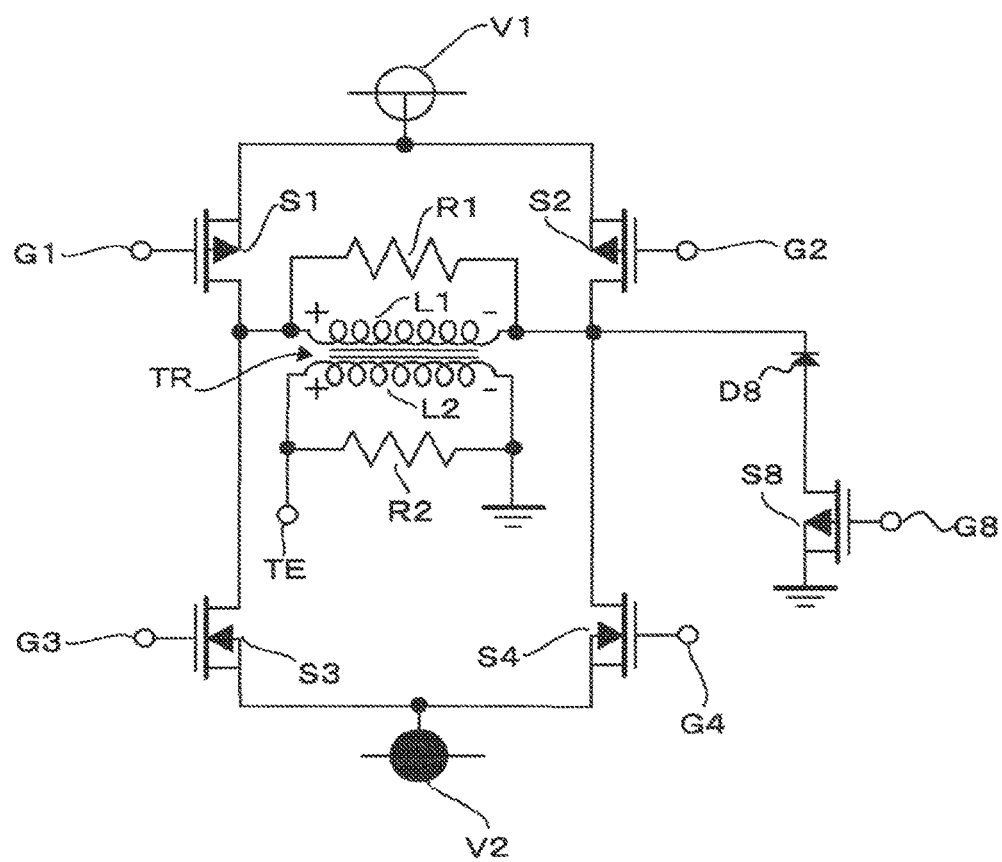
FIG. 9 is a circuit diagram illustrating the configuration of a transmitter circuit according to another modification of the embodiment.

This modification is different from the first embodiment and the modifications 1 and 2 thereof in the configuration of the switching unit of the transmitter circuit 10 and the transmission controller 11. In the following, the differences are described. FIGS. 9 and 3 are circuit diagrams illustrating the configuration of the transmitter circuit 10 of this modification. The terminal TE in FIG. 3 is connected to the terminal TE in FIG. 9.

The switching unit switches the connection path between the primary winding L1 and at least one of the first power source V1 and the second power source V2 to the first connection path that connects the first power source V1 to one end of the primary winding L1 and the second power source V2 to the other end of the primary winding L1, the second connection path that connects the first power source V1 to the other end of the primary winding L1 and the second power source V2 to the one end of the primary winding L1, the short circuit path that causes a short circuit between the one end and the other end of the primary winding L1, or the ground connection path that connects the first power source V1 or the second power source V2 to the ground through the primary winding L1, thereby generating voltages of different levels in the secondary winding L2. The ground connection path includes a fourth ground connection path, in which a current flows in order of the ground, the other end of the primary winding L1, the one end of the primary winding L1, and the second power source V2 as the forward direction.

The switching unit includes a pair of first potential-side switches, a pair of second potential-side switches, and a ground-side switch. The first potential-side switches are located between both ends of the primary winding L1 and the first power source V1. The switches S1 and S2 of this modification correspond to the first potential-side switches. The second potential-side switches are located between both ends of the primary winding L1 and the second power source V2. The switches S3 and S4 of this modification correspond to the second potential-side switches. The ground-side switch is located between the other end of the primary winding L1 and the ground. A switch S8 of this modification corresponds to the ground-side switch.

The first potential-side switches (the switches S1, S2) are field-effect transistors, in which a current flows from the first power source V1 side to the primary winding L1 side as the forward direction when they are on. More specifically, the first potential-side switches are so-called p-type MOSFETs. The second potential-side switches (the switches S3, S4) are field-effect transistors, in which a current flows from the primary winding L1 side to the second power source V2 side as the forward direction when they are on. More specifically, the second potential-side switches are so-called n-type MOSFETs. The ground-side switch (the switch S8) is arranged between the other end of the primary winding L1 and the ground in the fourth ground connection path. The ground-side switch is a field-effect transistor, in which a current flows from the ground side to the other end of the primary winding L1 side as the forward direction when it is on. More specifically, the ground-side switch is so-called p-type MOSFET.

The source of the switch S1 is connected to the first power source V1, and the drain of the switch S1 is connected to the one end of the primary winding L1. Besides, the source of the switch S2 is connected to the first power source V1, and the drain of the switch S2 is connected to the other end of the primary winding L1. The drain of the switch S3 is connected to the one end of the primary winding L1, and the source of the switch S3 is connected to the second power source V2. The drain of the switch S4 is connected to the other end of the primary winding L1, and the source of the switch S4 is connected to the second power source V2. The drain of the switch S8 is connected to the other end of the primary winding L1, and the source of the switch S8 is connected to the ground.

When the switching unit turns the switches S1 and S4 on and turns the switches S2, S3, and S8 off, and thereby switches the connection path to the first connection path, a voltage of "k×(V11−V21)" is generated in the secondary winding L2, and a transmission signal at this voltage level is sent to the ultrasound transducer 20. When the switching unit turns the switches S3 and S4 on and turns the switches S1, S2, and S8 off, and thereby switches the connection path to the short circuit path, the voltage of the primary winding L1 is zero, and also the voltage of the secondary winding L2 is zero. Thus, a transmission signal at this voltage level, i.e., zero voltage, is sent to the ultrasound transducer 20. Further, when the switching unit turns the switches S3 and S8 on and turns the switches S1, S2, and S4 off, and thereby switches the connection path to the fourth ground connection path, a voltage of "k×V21" is generated in the secondary winding L2, and a transmission signal at this voltage level is sent to the ultrasound transducer 20. Further, when the switching unit turns the switches S2 and S3 on and turns the switches S1, S4, and S8 off, and thereby switches the connection path to the second connection path, a voltage of "−k×(V11−V21)" is generated in the secondary winding L2, and a transmission signal at this voltage level is sent to the ultrasound transducer 20. Incidentally, the transmission signal is a signal with a reversed polarity of the transmission signal transmitted when the connection path is the first connection path. By switching the connection path in this manner, the transmitter circuit 10 can output transmission signals at four levels of voltages to the ultrasound transducer 20.

The transmitter circuit 10 may further include a diode D8 between the field-effect transistor (the switch S8) of the fourth ground connection path and the other end of the primary winding L1. The forward direction of the diode D8 is a direction from the ground to the other end of the primary winding L1. With this, the switch S8 can be protected from reverse voltage.

The transmission controller 11 outputs a control signal to the gate G1 of the switch S1, the gate G2 of the switch S2, the gate G3 of the switch S3, the gate G4 of the switch S4, and gate G8 of the switch S8 of the switching unit individually to turn on and off each of the switches S1, S2, S3, S4, and S8 individually.

[Operation]

Figure 10:
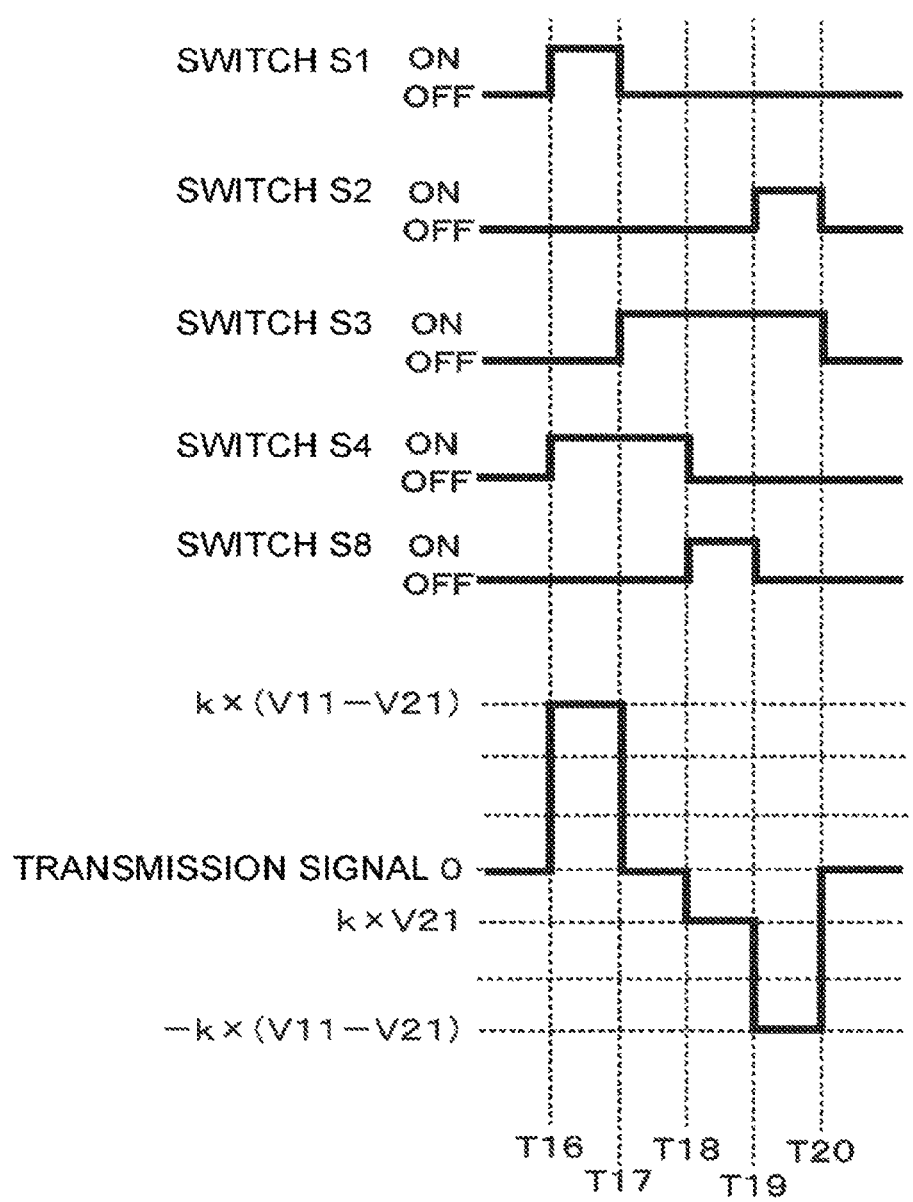
FIG. 10 is a timing chart illustrating an example of the operation of an ultrasound diagnosis apparatus of the modification.

FIG. 10 is a timing chart illustrating an example of the operation of the transmitter circuit 10 of the ultrasound diagnosis apparatus of this modification. The timing chart illustrates the relationship between the on/off state of each switch and the voltage level of the transmission signal.

From time T16 to time T17, according to a control signal from the transmission controller 11, the switching unit makes the switches S1 and S4 on, and makes the switches S2, S3, and S8 off. Thereby, the connection path is switched to the first connection path. At this time, a voltage of "k×(V11−V21)" is generated in the secondary winding L2, and a transmission signal at this voltage level is sent to the ultrasound transducer 20.

From time T17 to time T18, according to a control signal from the transmission controller 11, the switching unit makes the switches S3 and S4 on, and makes the switches S1, S2, and S8 off. Thereby, the connection path is switched to the short circuit path. At this time, the voltage of the primary winding L1 is zero, and also the voltage of the secondary winding L2 is zero. Thus, a transmission signal at this voltage level, i.e., zero voltage, is sent to the ultrasound transducer 20.

From time T18 to time T19, according to a control signal from the transmission controller 11, the switching unit makes the switches S3 and S8 on, and makes the switches S1, S2, and S4 off. Thereby, the connection path is switched to the fourth ground connection path. At this time, a voltage of "k×V21" is generated in the secondary winding L2, and a transmission signal at this voltage level is sent to the ultrasound transducer 20.

From time T19 to time T20, according to a control signal from the transmission controller 11, the switching unit makes the switches S2 and S3 on, and the switches S1, S4, and S8 off. Thereby, the connection path is switched to the second connection path. At this time, a voltage of "−k×(V11−V21)" is generated in the secondary winding L2, and a transmission signal at this voltage level is sent to the ultrasound transducer 20.

According to this modification, the ultrasound diagnosis apparatus includes a transformer TR, a first power source V1, a second power source V2, and a switching unit. The transformer TR is provided with a primary winding L1 and a secondary winding L2, and drives the ultrasound transducer 20 based on the voltage generated in the secondary winding L2. The switching unit switches the connection path between the primary winding L1 and at least one of the first power source V1 and the second power source V2 to the first connection path that connects the first power source V1 to one end of the primary winding L1 and the second power source V2 to the other end of the primary winding L1, the second connection path that connects the first power source V1 to the other end of the primary winding L1 and the second power source V2 to the one end of the primary winding L1, the short circuit path that causes a short circuit between the one end and the other end of the primary winding L1, or the ground connection path that connects the first power source V1 or the second power source V2 to the ground through the primary winding L1, thereby generating voltages of different levels in the secondary winding L2. The ground connection path includes the fourth ground connection path, in which a current flows in order of the ground, the other end of the primary winding L1, the one end of the primary winding L1, and the second power source V2 as the forward direction. Thus, the ultrasound diagnosis apparatus of this modification outputs transmission signals at various voltage levels from the transmitter circuit 10 that includes the one first power source V1 and the one second power source V2. Thereby, the small-scale transmitter circuit 10 can output transmission signals of different voltage levels to the ultrasound transducer 20.

In consideration of the circuit configuration among the first embodiment and its modifications described above, the ground connection path may include any combination of the first ground connection path, the second ground connection path, the third ground connection path, and the fourth ground connection path. A second embodiment is described below taking an example in which the ground connection path includes the first ground connection path, the second ground connection path, the third ground connection path, and the fourth ground connection path.

Second Embodiment

Figure 11:
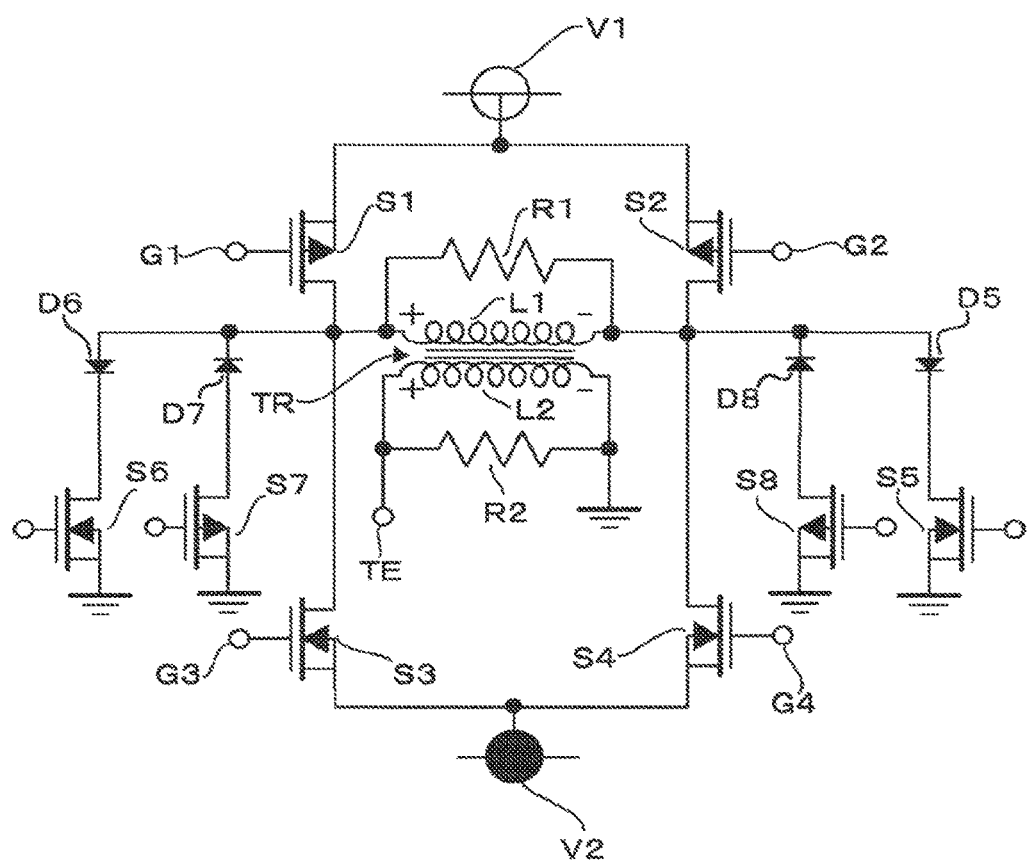
FIG. 11 is a circuit diagram illustrating the configuration of a transmitter circuit according to another embodiment.

An ultrasound diagnosis apparatus of the second embodiment is different from those of the first embodiment and the modifications 1 to 3 thereof in the configurations of the switching unit of the transmitter circuit 10 and the transmission controller 11. In the following, the differences are described. FIGS. 3 and 11 are circuit diagrams illustrating the configuration of the transmitter circuit 10 of this embodiment. The terminal TE in FIG. 3 is connected to the terminal TE in FIG. 9.

The switching unit switches the connection path between the primary winding L1 and at least one of the first power source V1 and the second power source V2 to the first connection path that connects the first power source V1 to one end of the primary winding L1 and the second power source V2 to the other end of the primary winding L1, the second connection path that connects the first power source V1 to the other end of the primary winding L1 and the second power source V2 to the one end of the primary winding L1, the short circuit path that causes a short circuit between the one end and the other end of the primary winding L1, or the ground connection path that connects the first power source V1 or the second power source V2 to the ground through the primary winding L1, thereby generating voltages of different levels in the secondary winding L2. The ground connection path includes the first ground connection path, in which a current flows in order of the first power source V1, the one end of the primary winding L1, the other end of the primary winding L1, and the ground as the forward direction. The ground connection path further includes the second ground connection path, in which a current flows in order of the first power source V1, the other end of the primary winding L1, the one end of the primary winding L1, and the ground as the forward direction. The ground connection path further includes the third ground connection path, in which a current flows in order of the ground, the one end of the primary winding L1, the other end of the primary winding L1, and the second power source V2 as the forward direction. The ground connection path still further includes the fourth ground connection path, in which a current flows in order of the ground, the other end of the primary winding L1, the one end of the primary winding L1, and the second power source V2 as the forward direction.

The switching unit includes a pair of first potential-side switches, a pair of second potential-side switches, and a ground-side switch. The first potential-side switches are located between both ends of the primary winding L1 and the first power source V1. The switches S1 and S2 of this embodiment correspond to the first potential-side switches. The second potential-side switches are located between both ends of the primary winding L1 and the second power source V2. The switches S3 and S4 of this embodiment correspond to the second potential-side switches. The ground-side switch includes the switches S5 and S8 located between the other end of the primary winding L1 and the ground, and the switches S6 and S7 located between the one end of the primary winding L1 and the ground. Note that the switches S5 and S8 are arranged in parallel with the primary winding L1. The switches S6 and S7 are also arranged in parallel with the primary winding L1.

The first potential-side switches (the switches S1, S2) are field-effect transistors, in which a current flows from the first power source V1 side to the primary winding L1 side as the forward direction when they are on. More specifically, the first potential-side switches are so-called p-type MOSFETs. The second potential-side switches (the switches S3, S4) are field-effect transistors, in which a current flows from the primary winding L1 side to the second power source V2 side as the forward direction when they are on. More specifically, the second potential-side switches are so-called n-type MOSFETs.

The switch S5 is arranged between the other end of the primary winding L1 and the ground in the first ground connection path. The switch S5 is a field-effect transistor, in which a current flows from the other end of the primary winding L1 side to the ground side as the forward direction when it is on. More specifically, the switch S5 is so-called n-type MOSFET. The switch S6 is arranged between the one end of the primary winding L1 and the ground in the second ground connection path. The switch S6 is a field-effect transistor, in which a current flows from the one end of the primary winding L1 side to the ground side as the forward direction when it is on. More specifically, the switch S6 is so-called n-type MOSFET. The switch S7 is arranged between the one end of the primary winding L1 and the ground in the third ground connection path. The switch S7 is a field-effect transistor, in which a current flows from the ground side to the one end of the primary winding L1 side as the forward direction when it is on. More specifically, the switch S7 is so-called p-type MOSFET. The switch S8 is arranged between the other end of the primary winding L1 and the ground in the fourth ground connection path. The switch S8 is a field-effect transistor, in which a current flows from the ground side to the other end of the primary winding L1 side as the forward direction when it is on. More specifically, the switch S8 is so-called p-type MOSFET.

The source of the switch S1 is connected to the first power source V1, and the drain of the switch S1 is connected to the one end of the primary winding L1. Besides, the source of the switch S2 is connected to the first power source V1, and the drain of the switch S2 is connected to the other end of the primary winding L1. The drain of the switch S3 is connected to the one end of the primary winding L1, and the source of the switch S3 is connected to the second power source V2. The drain of the switch S4 is connected to the other end of the primary winding L1, and the source of the switch S4 is connected to the second power source V2.

The drain of the switch S5 is connected to the other end of the primary winding L1, and the source of the switch S5 is connected to the ground. The drain of the switch S6 is connected to the one end of the primary winding L1, and the source of the switch S6 is connected to the ground. The drain of the switch S7 is connected to the one end of the primary winding L1, and the source of the switch S7 is connected to the ground. The drain of the switch S8 is connected to the other end of the primary winding L1, and the source of the switch S8 is connected to the ground.

When the switching unit turns the switches S1 and S4 on and turns the switches S2, S3, S5, S6, S7, and S8 off, and thereby switches the connection path to the first connection path, a voltage of "k×(V11−V21)" is generated in the secondary winding L2, and a transmission signal at this voltage level is sent to the ultrasound transducer 20. When the switching unit turns the switches S1 and S5 on and turns the switches S2, S3, S4, S6, S7, and S8 off, and thereby switches the connection path to the first ground connection path, a voltage of "k×V11" is generated in the secondary winding L2, and a transmission signal at this voltage level is sent to the ultrasound transducer 20. When the switching unit turns the switches S4 and S7 on and turns the switches S1, S2, S3, S5, S6 and S8 off, and thereby switches the connection path to the third ground connection path, a voltage of "−k×V21" is generated in the secondary winding L2, and a transmission signal at this voltage level is sent to the ultrasound transducer 20. Further, when the switching unit turns the switches S3 and S4 on and turns the switches S1, S2, S5, S6, S7, and S8 off, and thereby switches the connection path to the short circuit path, the voltage of the primary winding L1 is zero, and also the voltage of the secondary winding L2 is zero. Thus, a transmission signal at this voltage level, i.e., zero voltage, is sent to the ultrasound transducer 20. When the switching unit turns the switches S3 and S8 on and turns the switches S1, S2, S4, S5, S6, and S7 off, and thereby switches the connection path to the fourth ground connection path, a voltage of "k×V21" is generated in the secondary winding L2, and a transmission signal at this voltage level is sent to the ultrasound transducer 20. Incidentally, the transmission signal is a signal with a reversed polarity of the transmission signal transmitted when the connection path is the third ground connection path. Further, when the switching unit turns the switches S2 and S6 on and turns switches S1, S3, S4, S5, S7 and S8 off, and thereby switches the connection path to the second ground connection path, a voltage of "−k×V11" is generated in the secondary winding L2, and a transmission signal at this voltage level is sent to the ultrasound transducer 20. Incidentally, the transmission signal is a signal with a reversed polarity of the transmission signal transmitted when the connection path is the first ground connection path. Further, when the switching unit turns the switches S2 and S3 on and turns the switches S1, S4, S5, S6, S7, and S8 off, and thereby switches the connection path to the second connection path, a voltage of "−k×(V11−V21)" is generated in the secondary winding L2, and a transmission signal at this voltage level is sent to the ultrasound transducer 20. Incidentally, the transmission signal is a signal with a reversed polarity of the transmission signal transmitted when the connection path is the first connection path. By switching the connection path in this manner, the transmitter circuit 10 can output transmission signals at seven levels of voltages to the ultrasound transducer.

The transmitter circuit 10 may include the diode D5 between the field-effect transistor (the switch S5) of the first ground connection path and the other end of the primary winding L1. The forward direction of the diode D5 is a direction from the other end of the primary winding L1 to the ground. The transmitter circuit 10 may further include the diode D6 between the field-effect transistor (the switch S6) of the second ground connection path and the one end of the primary winding L1. The forward direction of the diode D6 is a direction from the one end of the primary winding L1 to the ground. The transmitter circuit 10 may further include the diode D7 between the field-effect transistor (the switch S7) of the third ground connection path and the one end of the primary winding L1. The forward direction of the diode D7 is a direction from the ground to the one end of the primary winding L1. The transmitter circuit 10 may still further include the diode D8 between the field-effect transistor (the switch S8) of the fourth ground connection path and the other end of the primary winding L1. The forward direction of the diode D8 is a direction from the ground to the other end of the primary winding L1. Thus, the diodes D5, D6, D7, and D8 protect the switches S5, S6, S7, and S8 from reverse voltage.

The transmission controller 11 outputs a control signal to the gate G1 of the switch S1, the gate G2 of the switch S2, the gate G3 of the switch S3, the gate G4 of the switch S4, gate G5 of the switch S5, the gate G6 of the switch S6, gate G7 of the switch S7, and the gate G8 of the switch S8 of the switching unit individually to turn on and off each of the switches S1, S2, S3, S4, S5, S6, S7, and S8 individually turned.

[Operation]

Figure 12:
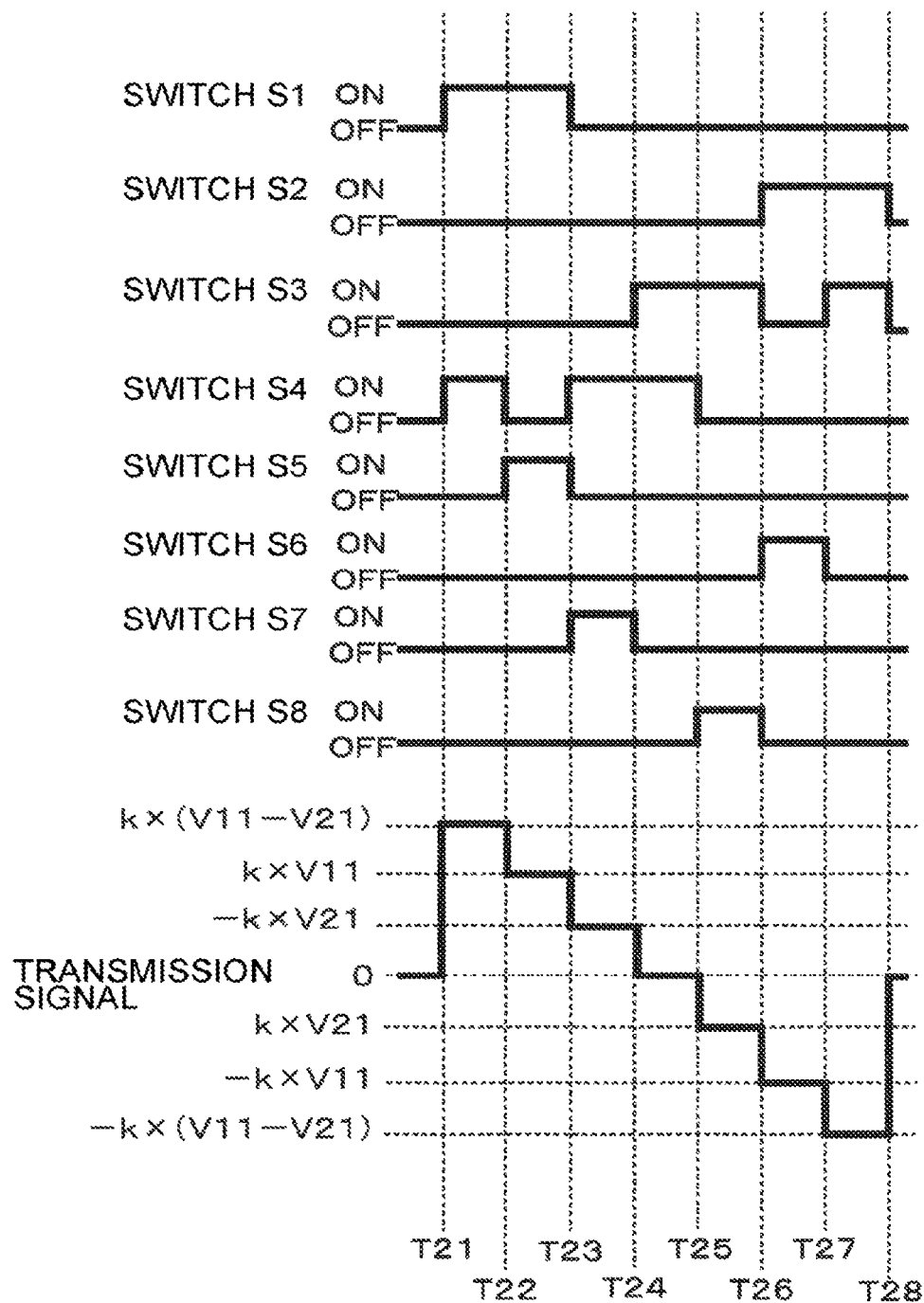
FIG. 12 is a timing chart illustrating an example of the operation of an ultrasound diagnosis apparatus of the embodiment.

FIG. 12 is a timing chart illustrating an example of the operation of the transmitter circuit 10 of the ultrasound diagnosis apparatus of this embodiment. The timing chart illustrates the relationship between the on/off state of each switch and the voltage level of the transmission signal.

From time T21 to time T22, according to a control signal from the transmission controller 11, the switching unit makes the switches S1 and S4 on, and makes the switches S2, S3, S5, S6, S7, and S8 off. Thereby, the connection path is switched to the first connection path. At this time, a voltage of "k×(V11−V21)" is generated in the secondary winding L2, and a transmission signal at this voltage level is sent to the ultrasound transducer 20.

From time T22 to time T23, according to a control signal from the transmission controller 11, the switching unit makes the switches S1 and S5 on, and makes the switches S2, S3, S4, S6, S7, and S8 off. Thereby, the connection path is switched to the first ground connection path. At this time, a voltage of "k×V11" is generated in the secondary winding L2, and a transmission signal at this voltage level is sent to the ultrasound transducer 20.

From time T23 to time T24, according to a control signal from the transmission controller 11, the switching unit makes the switches S4 and S7 on, and makes the switches S1, S2, S3, S5, S6, and S8 off. Thereby, the connection path is switched to the third ground connection path. At this time, a voltage of "−k×V21" is generated in the secondary winding L2, and a transmission signal at this voltage level is sent to the ultrasound transducer 20.

From time T24 to time T25, according to a control signal from the transmission controller 11, the switching unit makes the switches S3 and S4 on, and makes the switches S1, S2, S5, S6, S7, and S8 off. Thereby, the connection path is switched to the short circuit path. At this time, the voltage of the primary winding L1 is zero, and also the voltage of the secondary winding L2 is zero. Thus, a transmission signal at this voltage level, i.e., zero voltage, is sent to the ultrasound transducer 20.

From time T25 to time T26, according to a control signal from the transmission controller 11, the switching unit makes the switches S3 and S8 on, and makes the switches S1, S2, S4, S5, S6, and S7 off. Thereby, the connection path is switched to the fourth ground connection path. At this time, a voltage of "k×V21" is generated in the secondary winding L2, and a transmission signal at this voltage level is sent to the ultrasound transducer 20.

From time T26 to time T27, according to a control signal from the transmission controller 11, the switching unit makes the switches S2 and S6 on, and makes the switches S1, S3, S4, S5, S7, and S8 off. Thereby, the connection path is switched to the second ground connection path. At this time, a voltage of "−k×V11" is generated in the secondary winding L2, and a transmission signal at this voltage level is sent to the ultrasound transducer 20.

From time T27 to time T28, according to a control signal from the transmission controller 11, the switching unit makes the switches S2 and S3 on, and the switches S1, S4, S5, S6, S7, and S8 off. Thereby, the connection path is switched to the second connection path. At this time, a voltage of "−k×(V11−V21)" is generated in the secondary winding L2, and a transmission signal at this voltage level is sent to the ultrasound transducer 20.

According to this embodiment, the ultrasound diagnosis apparatus includes a transformer TR, a first power source V1, a second power source V2, and a switching unit. The transformer TR is provided with a primary winding L1 and a secondary winding L2, and drives the ultrasound transducer 20 based on the voltage generated in the secondary winding L2. The switching unit switches the connection path between the primary winding L1 and at least one of the first power source V1 and the second power source V2 to the first connection path that connects the first power source V1 to one end of the primary winding L1 and the second power source V2 to the other end of the primary winding L1, the second connection path that connects the first power source V1 to the other end of the primary winding L1 and the second power source V2 to the one end of the primary winding L1, the short circuit path that causes a short circuit between the one end and the other end of the primary winding L1, or the ground connection path that connects the first power source V1 or the second power source V2 to the ground through the primary winding L1, thereby generating voltages of different levels in the secondary winding L2. The ground connection path includes the first ground connection path, in which a current flows in order of the first power source V1, the one end of the primary winding L1, the other end of the primary winding L1, and the ground as the forward direction. The ground connection path further includes the second ground connection path, in which a current flows in order of the first power source V1, the other end of the primary winding L1, the one end of the primary winding L1, and the ground as the forward direction. The ground connection path further includes the third ground connection path, in which a current flows in order of the ground, the one end of the primary winding L1, the other end of the primary winding L1, and the second power source V2 as the forward direction. The ground connection path still further includes the fourth ground connection path, in which a current flows in order of the ground, the other end of the primary winding L1, the one end of the primary winding L1, and the second power source V2 as the forward direction. Thus, the ultrasound diagnosis apparatus of this embodiment outputs transmission signals at various voltage levels from the transmitter circuit 10 that includes the one first power source V1 and the one second power source V2. Thereby, the small-scale transmitter circuit 10 can output transmission signals of different voltage levels to the ultrasound transducer 20.

Other Embodiments

Figure 13:
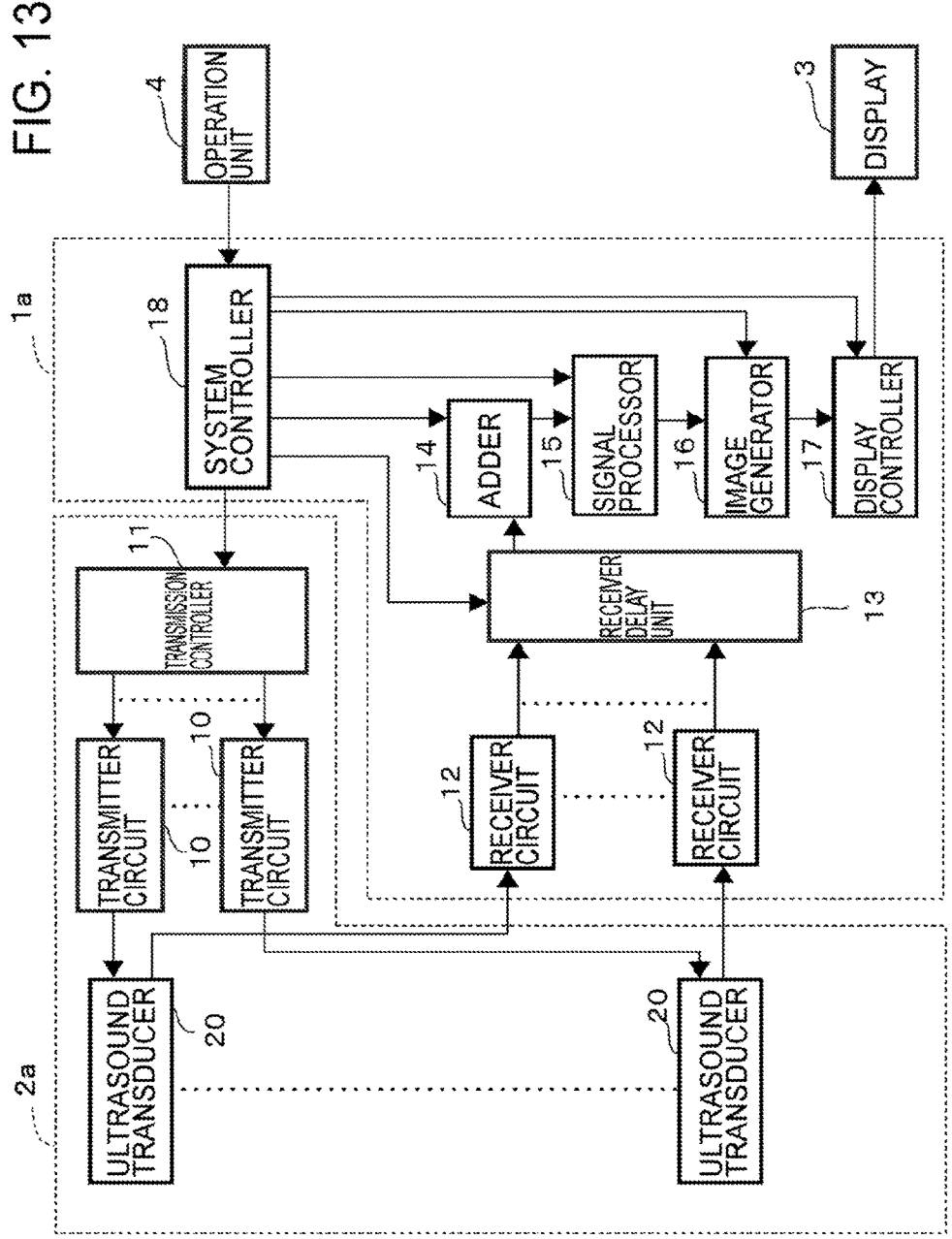
FIG. 13 is a block diagram illustrating the configuration of an ultrasound diagnosis apparatus according to another embodiment.

FIG. 13 is a block diagram illustrating a configuration of an ultrasound probe according to this embodiment. This embodiment is different from the above embodiments and the modifications thereof in the arrangement of the transmitter circuit 10 and the transmission controller 11. In this embodiment, the transmitter circuit 10 and the transmission controller 11 are arranged in an ultrasound probe 2a. The transmitter circuit 10 and the transmission controller 11 may be located anywhere in the probe head of the ultrasound probe 2a, a connector to be connected to a main body 1a, and a cable connecting the probe head and the connector. The transmission controller 11 operates according to control signals from the main body 1a of the embodiment. The transmitter circuit 10 and the transmission controller 11 may operate as in any of the first and second embodiments and the modifications 1 to 3 thereof.

According to at least one of the embodiments described above, the ultrasound diagnosis apparatus or the ultrasound probe includes a transformer TR, a first power source V1, a second power source V2, and a switching unit. The transformer TR is provided with a primary winding L1 and a secondary winding L2, and drives the ultrasound transducer 20 based on the voltage generated in the secondary winding L2. The switching unit switches the connection path between the primary winding L1 and at least one of the first power source V1 and the second power source V2 to the first connection path that connects the first power source V1 to one end of the primary winding L1 and the second power source V2 to the other end of the primary winding L1, the second connection path that connects the first power source V1 to the other end of the primary winding L1 and the second power source V2 to the one end of the primary winding L1, the short circuit path that causes a short circuit between the one end and the other end of the primary winding L1, or the ground connection path that connects the first power source V1 or the second power source V2 to the ground through the primary winding L1, thereby generating voltages of different levels in the secondary winding L2. Thus, the ultrasound diagnosis apparatus of the embodiment(s) outputs transmission signals at various voltage levels from the transmitter circuit 10 that includes the one first power source V1 and the one second power source V2. Thereby, the small-scale transmitter circuit 10 can output transmission signals of different voltage levels to the ultrasound transducer 20.

Moreover, by utilizing the fact that the transmitter circuit is capable of outputting transmission signals at various voltage levels, interference can be reduced between a reception signal and the remaining components of a transmission signal that may be present in the downstream of the diode switch in the circuit of FIG. 3. During the operation of the ultrasound diagnosis apparatus, the ultrasound transducer may sometimes receive ultrasound waves and output echo signals while the end part of transmission signals remains in the downstream of the secondary winding. In this case, in the downstream of the diode switch in the circuit of FIG. 3, the remaining components of transmission signals may interfere with reception signals, and noise may occur in a signal to be received by the receiver circuit. The higher the voltage level of the remaining components of transmission signals, the higher the noise. The ultrasound diagnosis apparatus or the ultrasound probe of at least one of the embodiments and the modifications described above can reduce the interference between the remaining components of a transmission signal and a reception signal by, for example, lowering the voltage level of the reception signal for the transmission signal.

Further, by utilizing the fact that the transmitter circuit is capable of outputting transmission signals at various voltage levels, ultrasound waves can be transmitted simultaneously in parallel to a plurality of focal points. For example, to transmit ultrasound waves to two focal points, the transmitter circuit combines a transmission signal to one of the focal points and a transmission signal to the other into one signal based on transmission delay time for each of the focal points and outputs the signal to the ultrasound transducer. The signal generally has a step-like waveform. According to the embodiment(s), transmission signals at various voltage levels can be transmitted. Therefore, by outputting such a transmission signal that enables the output of a combined transmission signal to each ultrasound transducer, ultrasound waves are focused simultaneously and in parallel at the focal points. Thus, the ultrasound diagnosis apparatus or the ultrasound probe of the embodiment(s) can transmit ultrasound waves to a plurality of focal points simultaneously in parallel.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasound diagnosis apparatus, comprising:
a transformer including a primary winding and a secondary winding, and configured to drive an ultrasound transducer based on a voltage generated in the secondary winding;
a first power source configured to cause a potential difference with respect to a reference potential of ground at a first potential that is different from the reference potential;
a second power source configured to cause a potential difference with respect to the reference potential at a second potential that is different from the reference potential and the first potential; and
a switching unit configured to switch a connection path between the primary winding and at least one of the first power source and the second power source to a first connection path that connects the first power source to one end of the primary winding and the second power source to another end of the primary winding, a second connection path that connects the first power source to the other end of the primary winding and the second power source to the one end of the primary winding, or a ground connection path that connects the first power source or the second power source to the ground through the primary winding.

2. The ultrasound diagnosis apparatus of claim 1, wherein the switching unit is further configured to be capable of switching the connection path to a short circuit path that causes a short circuit between the one end and the other end of the primary winding.

3. The ultrasound diagnosis apparatus of claim 1, wherein
the first power source has the first potential that is higher than the reference potential to cause the potential difference, and
the second power source has the second potential that is lower than the reference potential to cause the potential difference.

4. The ultrasound diagnosis apparatus of claim 1, wherein the ground connection path includes
a first ground connection path, in which a current flows in order of the first power source, the one end of the primary winding, the other end of the primary winding, and the ground as a forward direction,
a second ground connection path, in which a current flows in order of the first power source, the other end of the primary winding, the one end of the primary winding, and the ground as a forward direction,
a third ground connection path, in which a current flows in order of the ground, the one end of the primary winding, the other end of the primary winding, and the second power source as a forward direction,
a fourth ground connection path, in which a current flows in order of the ground, the other end of the primary winding, the one end of the primary winding, and the second power source as a forward direction, or
any combination of two or three of the first to fourth ground connection paths.

5. The ultrasound diagnosis apparatus of claim 1, wherein the ground connection path includes
a first ground connection path, in which a current flows in order of the first power source, the one end of the primary winding, the other end of the primary winding, and the ground as a forward direction,
a second ground connection path, in which a current flows in order of the first power source, the other end of the primary winding, the one end of the primary winding, and the ground as a forward direction,
a third ground connection path, in which a current flows in order of the ground, the one end of the primary winding, the other end of the primary winding, and the second power source as a forward direction, and
a fourth ground connection path, in which a current flows in order of the ground, the other end of the primary winding, the one end of the primary winding, and the second power source as a forward direction.

6. The ultrasound diagnosis apparatus of claim 4, wherein the switching unit includes
first potential-side switches, each located between the one end or the other end of the primary winding and the first power source,
second potential-side switches, each located between the one end or the other end of the primary winding and the second power source, and
a ground-side switch located between the one end or the other end of the primary winding and the ground.

7. The ultrasound diagnosis apparatus of claim 6, wherein the first potential-side switches are field-effect transistors, in which a current flows from first power source side to primary winding side as a forward direction when the first potential-side switches are on,
the second potential-side switches are field-effect transistors, in which a current flows from the primary winding side to second power source side as a forward direction when the second potential-side switches are on, and
the ground-side switch includes
a field-effect transistor located between the other end of the primary winding and the ground in the first ground connection path, in which a current flows from the other end of the primary winding side to ground side as a forward direction when the transistor is on,
a field-effect transistor located between the one end of the primary winding and the ground in the second ground connection path, in which a current flows from the one end of the primary winding side to the ground side as a forward direction when the transistor is on,
a field-effect transistor located between the ground and the one end of the primary winding in the third ground connection path, in which a current flows from the ground side to the one end of the primary winding side as a forward direction when the transistor is on, and
a field-effect transistor located between the ground and the other end of the primary winding in the fourth ground connection path, in which a current flows from the ground side to the other end of the primary winding side as a forward direction when the transistor is on.

8. The ultrasound diagnosis apparatus of claim 7, further comprising:
a diode located between the field-effect transistor of the first ground connection path and the other end of the primary winding, forward direction of which is a direction from the other end of the primary winding to the ground;
a diode located between the field-effect transistor of the second ground connection path and the one end of the primary winding, forward direction of which is a direction from the one end of the primary winding to the ground;
a diode located between the field-effect transistor of the third ground connection path and the one end of the primary winding, forward direction of which is a direction from the ground to the one end of the primary winding; and
a diode located between the field-effect transistor of the fourth ground connection path and the other end of the primary winding, forward direction of which is a direction from the ground to the other end of the primary winding.

9. An ultrasound diagnosis apparatus, comprising:
a transformer including a primary winding and a secondary winding, and configured to drive an ultrasound transducer based on a voltage generated in the secondary winding;
a first power source configured to cause a potential difference with respect to a reference potential of ground at a first potential that is different from the reference potential;
a second power source configured to cause a potential difference with respect to the reference potential at a second potential that is different from the reference potential and the first potential;
a pair of first potential-side switches, each located between one end or another end of the primary winding and the first power source, configured to be capable of turning on and off a connection between both ends of the primary winding and the first power source;
a pair of second potential-side switches, each located between the one end or the other end of the primary winding and the second power source, configured to be capable of turning on and off a connection between the both ends of the primary winding and the second power source; and
a ground-side switch located between the one end, the other end, or the both ends of the primary winding and the ground, configured to be capable of turning on and off a connection between the primary winding and the ground.

10. The ultrasound diagnosis apparatus of claim 9, wherein
the first potential-side switches are p-type MOSFETs, in which a current flows from first power source side to primary winding side as a forward direction when the first potential-side switches are on,
the second potential-side switches are n-type MOSFETs, in which a current flows from the primary winding side to second power source side as a forward direction when the second potential-side switches are on, and
the ground-side switch includes
an n-type MOSFET located between the other end of the primary winding and the ground, in which a current flows from the other end of the primary winding side to ground side as a forward direction when the MOSFET is on,
an n-type MOSFET located between the one end of the primary winding and the ground, in which a current flows from the one end of the primary winding side to the ground side as a forward direction when the MOSFET is on,
a p-type MOSFET located between the ground and the one end of the primary winding, in which a current flows from the ground side to the one end of the primary winding side as a forward direction when the MOSFET is on, a p-type MOSFET located between the ground and the other end of the primary winding, in which a current flows from the ground side to the other end of the primary winding side as a forward direction when the MOSFET is on, or any combination of the MOSFETs.

11. An ultrasound probe, comprising:

an ultrasound transducer;

a transformer including a primary winding and a secondary winding, and configured to drive the ultrasound transducer based on a voltage generated in the secondary winding;

a first power source configured to cause a potential difference with respect to a reference potential of ground at a first potential that is different from the reference potential;

a second power source configured to cause a potential difference with respect to the reference potential at a second potential that is different from the reference potential and the first potential; and a switching unit configured to switch a connection path between the primary winding and at least one of the first power source and the second power source to a first connection path that connects the first power source to one end of the primary winding and the second power source to another end of the primary winding, a second connection path that connects the first power source to the other end of the primary winding and the second power source to the one end of the primary winding, or a ground connection path that connects the first power source or the second power source to the ground through the primary winding.

12. An ultrasound probe, comprising:

an ultrasound transducer;

a transformer including a primary winding and a secondary winding, and configured to drive the ultrasound transducer based on a voltage generated in the secondary winding;

a first power source configured to cause a potential difference with respect to a reference potential of ground at a first potential that is different from the reference potential;

a second power source configured to cause a potential difference with respect to the reference potential at a second potential that is different from the reference potential and the first potential;

a pair of first potential-side switches, each located between one end or another end of the primary winding and the first power source, configured to be capable of turning on and off a connection between both ends of the primary winding and the first power source;

a pair of second potential-side switches, each located between the one end or the other end of the primary winding and the second power source, configured to be capable of turning on and off a connection between the both ends of the primary winding and the second power source; and a ground-side switch located between the one end, the other end, or the both ends of the primary winding and the ground, configured to be capable of turning on and off a connection between the primary winding and the ground.

* * * * *